United States Patent
Nagler et al.

(10) Patent No.: US 9,075,060 B2
(45) Date of Patent: Jul. 7, 2015

(54) METHODS FOR DIAGNOSING ORAL OR ORAL-PHARYNGEAL CANCER

(75) Inventors: Rafael M. Nagler, Timrat (IL); Moshe Gavish, Tel-Aviv (IL)

(73) Assignee: Technion Research & Development Foundation Limited, Haifa (IL)

( * ) Notice: Subject to any disclaimer, the term of this patent is extended or adjusted under 35 U.S.C. 154(b) by 594 days.

(21) Appl. No.: 12/816,482

(22) Filed: Jun. 16, 2010

(65) Prior Publication Data

US 2010/0317040 A1 Dec. 16, 2010

Related U.S. Application Data

(60) Provisional application No. 61/213,525, filed on Jun. 16, 2009.

(51) Int. Cl.
*G01N 33/574* (2006.01)

(52) U.S. Cl.
CPC .... *G01N 33/57407* (2013.01); *G01N 33/57488* (2013.01)

(58) Field of Classification Search
CPC ............... G01N 2800/18; G01N 33/57407
See application file for complete search history.

(56) References Cited

U.S. PATENT DOCUMENTS

| | | | |
|---|---|---|---|
| 5,776,946 A | 7/1998 | McGeer et al. | |
| 6,686,354 B2 | 2/2004 | Joly et al. | |
| 6,767,533 B1 | 7/2004 | Casellas et al. | |
| 6,986,995 B2 | 1/2006 | Rose et al. | |
| 7,220,739 B2 | 5/2007 | Glick et al. | |
| 7,267,977 B2 | 9/2007 | Papadopoulos et al. | |
| 7,731,938 B2 | 6/2010 | Karl et al. | |
| 2010/0021928 A1 | 1/2010 | Nagler et al. | |

FOREIGN PATENT DOCUMENTS

| WO | WO 2005/081867 | 9/2005 |
|---|---|---|
| WO | WO 2005/095987 | 10/2005 |
| WO | WO 2006/115302 | 11/2006 |
| WO | WO 2008/001357 | 1/2008 |
| WO | WO 2008/023357 | 2/2008 |
| WO | WO 2009/004621 | 1/2009 |

OTHER PUBLICATIONS de Vicente et al. (Oral Oncology 2002 38: 301-308).*
Cervigne et al. (2009 AACR Annual Meeting, Apr. 19, 2009, Abstract #573).*
Shiptzer et al. (British J. Cancer Sep. 29, 2009 101:1194-1198).*
Nagler et al. (Biochimica et Biphysica Acta Jan. 18, 2010 1802: 454-461).*
Nagler et al. ( Biochimica et Biophysica Acta Jan. 18, 2010 1802: 454-461).*
Medical Dictionary (risk, http://www.medicaldictionaryweb.com/Risk-definition/ downloaded Feb. 16, 2015).*
Response Dated Nov. 8, 2011 to Official Action of Sep. 8, 2011 From the US Patent and Trademark Office Re. U.S. Appl. No. 12/306,548.
Communication Relating to the Results of the Partial International Search Dated Oct. 9, 2007 From the International Searching Authority Re.: Application No. PCT/IL2007/000769.
International Search Report and the Written Opinion Dated Feb. 5, 2008 From the International Searching Authority Re. Application No. PCT/IL2007/000769.
Galiègue et al. "Immunohistochemical Assessment of the Peripheral Benzodiazepine Receptor in Breast Cancer and Its Relationship With Survival", Clinical Cancer Research, 10: 2058-2064, Mar. 15, 2004.
Han et al. Expression of Peripheral Benzodiazepine Receptor (PBR) in Human Tumors: Relationship to Breast, Colorectal, and Prostate Tumor Progression, Journal of Receptors and Signal Transduction, 23(2 & 3): 225-238, 2003.
Paz-Elizur et al. "Reduced Repair of the Oxidative 8-Oxoguanine DNA Damage and Risk of Head and Neck Cancer", Cancer Research, 66(24): 11683-11689, Dec. 15, 2006.
Rhodus et al. "NF-κB Dependent Cytokine Levels in Saliva of Patients With Oral Preneoplastic Lesions and Oral Squamous Cell Carcinoma", Cancer Detection and Prevention, 29(1): 42-45, 2005. Abstract.
Notice of Non-Compliant Amendment Dated May 14, 2012 From the US Patent and Trademark Office Re. U.S. Appl. No. 12/306,548.
Nagler et al. "Cigarette Smoke Decreases Salivary 18 kDa Translocator Protein Binding Affinity—in Associateion With Oxidative Stress", Current Medicinal Chemistry, 17(21): 1-8, 2010.
Response Dated Sep. 13, 2010 to Communication Pursuant to Article 94(3) EPC of May 12, 2010 From the European Patent Office Re. Application No. 07766801.0.
Communication Pursuant to Article 94(3) EPC Dated Oct. 11, 2011 From the European Patent Office Re. Application No. 07766801.0.
Official Action Dated Dec. 12, 2011 From the US Patent and Trademark Office Re. U.S. Appl. No. 12/306,548.
Negri et al. "Serum and Salivary CEA and GICA Levels in Oral Cavity Tumours", The International Journal of Biological Markers, 3(2): 107-112, 1988.
Zhong et al. "Detection of Cyfra 21-1 in Serum and Saliva From Patients With Oral Squamous Cell Carcinoma", Oral Oncology, 1(Suppl.): 179-180, Abstract #P111, Apr. 2005.
Communication Under Rule 71(3) EPC Dated Mar. 28, 2012 From the European Patent Office Re. Application No. 07766801.0.
International Preliminary Report on Patentability Dated Jan. 15, 2009 From the International Bureau of WIPO Re.: Application No. PCT/IL2007/000769.
Communication Pursuant to Article 94(3) EPC Dated May 12, 2010 From the European Patent Office Re. Application No. 07766801.0.

(Continued)

Primary Examiner — Peter J Reddig

(57) ABSTRACT

A method of diagnosing oral cancer or oral pharyngeal cancer in a subject in need thereof is provided. The method comprising determining a level or activity of at least one marker in a saliva sample of the subject, wherein a significant alteration in the level or the activity of the marker with respect to an unaffected saliva sample is indicative of the cancer, wherein the saliva marker is selected from the group consisting of Cyclin D1, phospho-Src, 8-oxoguanine DNA glycosylase (OGG1), Maspin, KI67 and translocator protein 18 kDa (TSPO).

13 Claims, 10 Drawing Sheets
(3 of 10 Drawing Sheet(s) Filed in Color)

(56) References Cited

OTHER PUBLICATIONS

Balakrishnan et al. "Antioxidant Properties of Hesperidin in Nicotine-Induced Lung Toxicity", Fundamental & Clinical Pharmacology, 21(5): 535-546, Oct. 2007. Abstract.
Barak et al. "Clinical Utility of Cytokeratins as Tumor Markers", Clinical Biochemistry, 37(7): 529-540, 2004. p. 531, col. 1, § 3-col. 2, § 1.
Brik et al. "Salivary Gland Involvement and Oxidative Stress in Juvenile Idiopathic Arthritis: Novel Observation in Oligoarticular-Type Patients", The Journal of Rheumatology, 33(12): 2532-2537, 2006.
Chen et al. "Src Family Kinases Mediate Betel Quid-Induced Oral Cancer Cell Motility and Could Be a Biomarker for Early Invasion in Oral Squamous Cell Carcinoma 1", Neoplasia, 10(12): 1393-1401, 2008.
Gattorno et al. "Serum and Synovial Fluid Concentrations of Matrix Metalloproteinases 3 and Its Tissue Inhibitor 1 in Juvenile Idiopathic Arthritis", The Journal of Rheumatology, 29(4): 826-831, Apr. 2002. Abstract.
Gattorno et al. "Synovial Membrane Expression of Matrix Metalloproteinases and Tissue Inhibitors 1 in Juvenile Idiopathic Arthritides", Journal of Rheumatology, 29(8): 1774-1779, Aug. 2002. Abstract.
Gavish et al. "Enigma of the Peripheral Benzodiazepine Receptor", Pharmacological Reviews, 51(4): 629-650, 1999.
Hirai et al. "Effects of Nitric Oxide on Matrix Metalloproteinase-2 Production by Rheumatoid Synovial Cells", Life Sciences, 68(8): 913-920, Jan. 12, 2001.
Katz et al. "Increase in Peripheral Benzodiazepine Binding Sites in Colonic Adenocarcinoma", Oncology, 47: 139-142, 1990.
Katz et al. "Increased Density of Peripheral Benzodiazepine-Binding Sites in Ovarian Carcinomas as Compared With Benign Ovarian Tumours and Normal Ovaries", Clinical Science, 78: 155-158, 1990.
Kawakubo et al. "Alterations of p53, Cyclin D1 and pRB Expression in the Carcinogenesis of Esophageal Squamous Cell Carcinoma", Oncology Reports, 14(6): 1453-1459, Dec. 2005. Abstract.
Kugler et al. "Ligands of the Mitochondrial 18 kDa Translocator Protein Attenuate Apoptosis of Human Glioblastoma Cells Exposed to Erucylphosphohomocholine", Cellular Oncology, 30: 435-450, 2008.
Liu et al. "Predictive Value of the Fraction of Cancer Cells Immunolabeled for Proliferating Cell Nuclear Antigen or Ki67 in Biopsies of Head and Neck Carcinomas to Identify Lymph Node Metastasis: Comparison With Clinical and Radiologic Examinations", Head & Neck, 25(4): 280-288, 2003.
Maaser et al. "Specific Ligands of the Peripheral Benzodiazepine Receptor Induce Apoptosis and Cell Cycle Arrest in Human Colorectal Cancer Cells", British Journal of Cancer, 85(11): 1771-1780, 2001.
Maaser et al. "Up-Regulation of the Peripheral Benzodiazepine Receptor During Human Colorectal Carcinogenesis and Tumor Spread", Clinical Cancer Research, 11: 1751-1756, Mar. 1, 2005.
Markkanen et al. "Assessment of Labial Salivary Gland Changes in Patients With Rheumatoid Arthritis by Subjective and Quantitative Methods", Applied Pathology, 7(4): 233-240, 1989. Abstract.
Mizukawa et al. "Defensin-1, A Peptide Detected in the Saliva of Oral Squamous Cell Carcinoma Patients", Anticancer Research, 18(6B): 4645-4649, 1998. Abstract. p. 4645, col. 2, § 2.

Nagler et al. "Concomitant Analysis of Salivary Tumor Markers—A New Diagnostic Tool for Oral Cancer", Clinical Cancer Research, 12(13): 3979-3984, 2006.
Nagler et al. "Early Diagnosis and Treatment Monitoring Roles of Tumor Markers Cyfra 21-1 and TPS in Oral Squamous Cell Carcinoma", Cancer, 85(5): 1018-1025, 1999. p. 1019, col. 2, § 3.
Nagler et al. "Salivary Gland Involvement in Rheumatoid Arthritis and Its Relationship to Induced Oxidative Stress", Rheumatology, 42(10): 1231-1241, 2003.
Peake et al. "Assessment of the Clinical Significance of Gelatinase Activity in Patients With Juvenile Idiopathic Arthritis Using Quantitative Protein Substrate Zymography", Annals of the Rheumatic Diseases, 65(4): 501-507, 2006.
Peake et al. "Levels of Matrix Metalloproteinase (MMP)-1 in Paired Sera and Synovial Fluids of Juvenile Idiopathic Arthritis Patients: Releationship to Inflammatory Activity, MMP-3 and Tissue Inhibitor of Metalloproteinases-1 in a Longitudinal Study", Rheumatology, 44(11): 1383-1389, 2005.
Rhodos et al. "NF-κB Dependent Cytokine Levels in Saliva of Patients With Oral Preneoplastic Lesions and Oral Squamous Cell Carcinoma", Cancer Detection and Prevention, 29(1): 42-45, 2005. Abstract.
Sathyan et al. "Influence of Single Nucleotide Polymorphisms in H-Ras and Cyclin D1 Genes on Oral Cancer Susceptibility", Oral Oncology, 42(6): 607-613, Jul. 2006.
Shoukrun et al. "The 18-kDa Translocator Protein, Formerly Known as the Peripheral-Type Benzodiazepine Receptor, Confers Proapoptotic and Antineoplastic Effects in a Human Colorectal Cancer Cell Line", Pharmacogenetics and Genomics, 18(11): 977-988, 2008.
Sullivan et al. "Impairment of Lachrymal and Salivary Secretion and Cellular Immune Responses to Salivary Antigens in Rheumatoid Arthritis", Annals of the Rheumatic Diseases, 37: 164-167, 1978.
Vairaktaris et al. "A Metalloproteinase-9 Polymorphism Which Affects Its Expression Is Associated With Increased Risk for Oral Squamous Cell Carcinoma", European Journal of Surgical Oncology, 34(4): 450-455, Apr. 2008. Abstract.
Van Oijen et al. "Overexpression of C-Src in Areas of Hyperproliferation in Head and Neck Cancer, Premalignant Lesions and Benign Mucosal Disorders", Journal of Oral Pathology & Medicine, 27(4): 147-152, Apr. 1998.
Veenman et al. "Peripheral-Type Benzodiazepine Receptor Density and In Vitro Tumorigenicity of Glioma Cell Lines", Biochemical Pharmacology, 68: 689-698, 2004.
Walton et al. "Sialochemistry in Juvenile Idiopathic Arthritis", Oral Diseases, 8(6): 287-290, Nov. 2002.
Wang et al. "Activation of ERK1/2 and Cyclin D1 Expression in Oral Tongue Squamous Cell Carcinomas: Relationship Between Clinicopathological Appearances and Cell Proliferation", Oral Oncology, 42(6): 625-631, 2006. Abstract.
Weisinger et al. "Peripheral Benzodiazepine Receptor Antisense Knockout Increases Tumorigenicity of MA-10 Leydig Cells In Vivo and In Vitro", Biochemistry, 43: 12315-12321, 2004.
Xia et al. "High Tumoral Maspin Expression Is Associated With Improved Survival of Patients With Oral Squamous Cell Carcinoma", Oncogene, 19: 2398-2403, 2000.
Yasumatsu et al. "Maspin Expression in Stage I and II Oral Tongue Squamous Cell Carcinoma", Head & Neck, 23(11): 962-966, Nov. 2001.
Official Action Dated Sep. 8, 2011 From the US Patent and Trademark Office Re. U.S. Appl. No. 12/306,548.

* cited by examiner

FIGs. 1A-B
A.
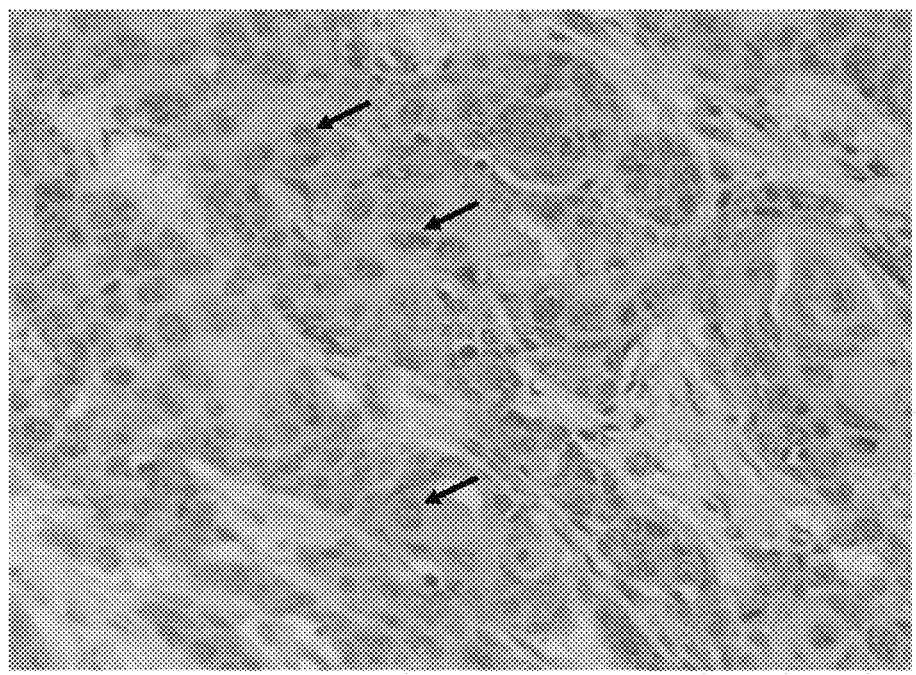
B.
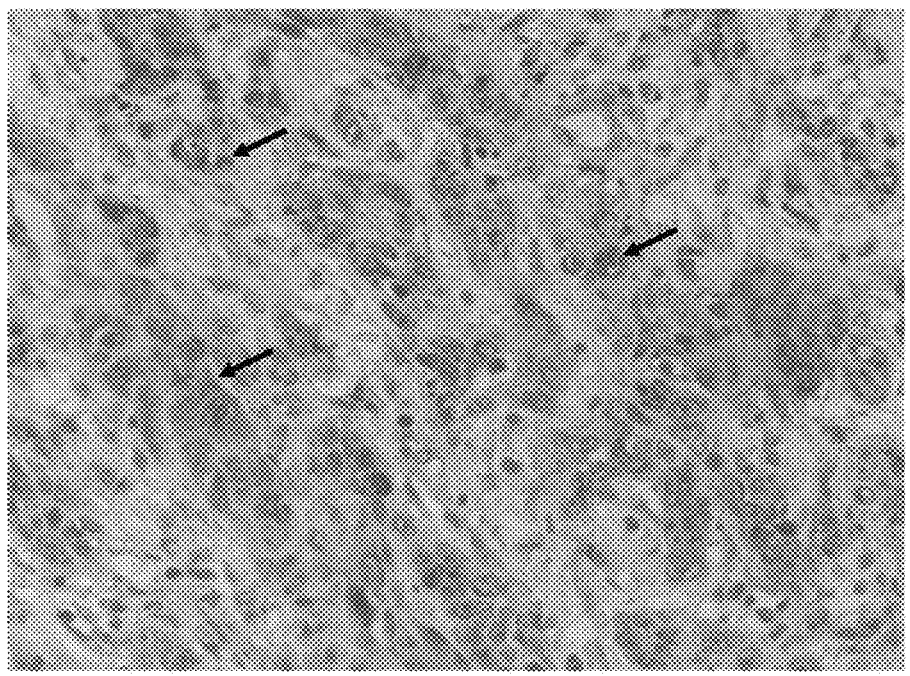

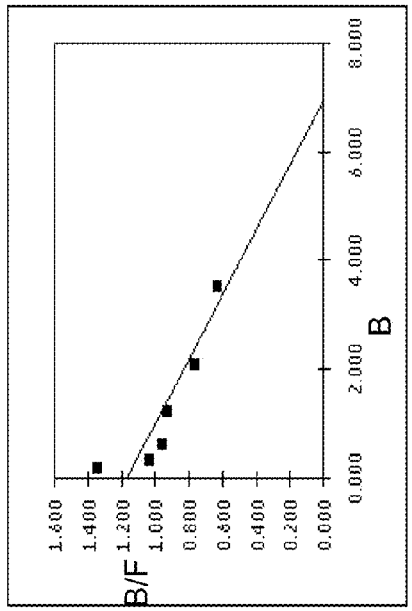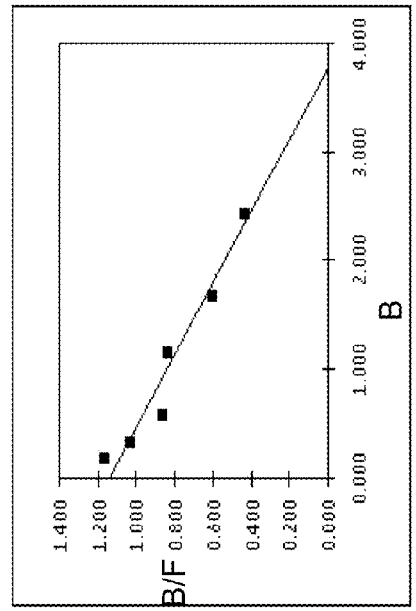
FIG. 4A
FIG. 4B

FIGs. 6A-B
A.
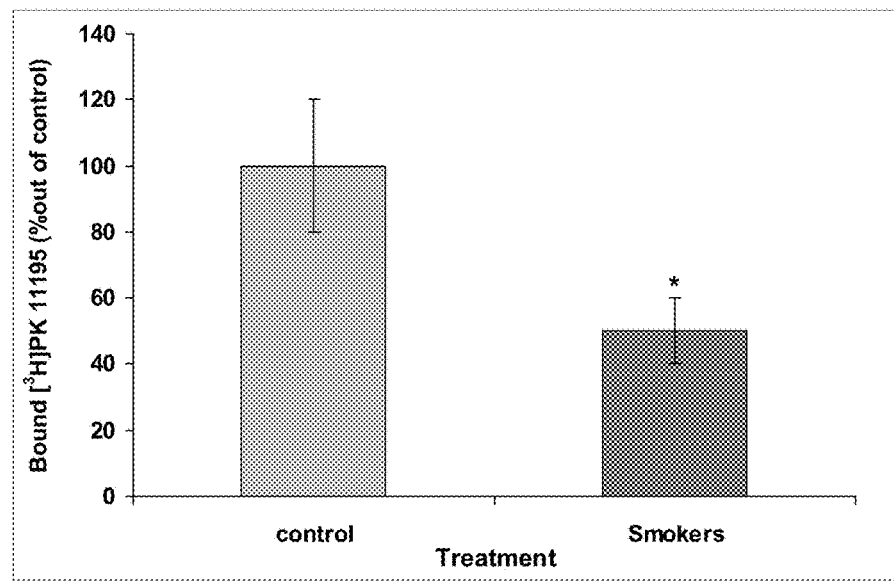
B.
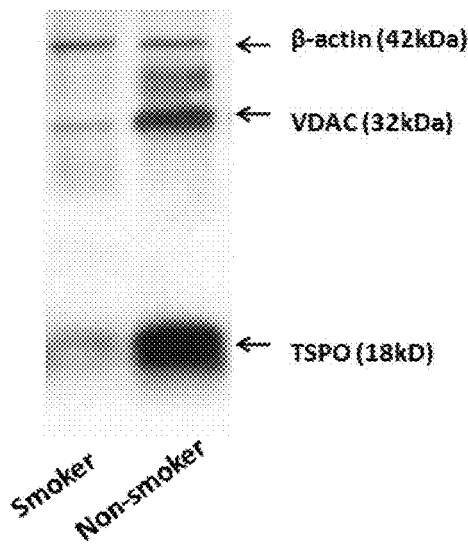

SEQUENCE LISTING

```
<160> NUMBER OF SEQ ID NOS: 15

<210> SEQ ID NO 1
<211> LENGTH: 295
<212> TYPE: PRT
<213> ORGANISM: Homo sapiens
```

<400> SEQUENCE: 1

```
Met Glu His Gln Leu Leu Cys Cys Glu Val Glu Thr Ile Arg Arg Ala
1               5                   10                  15

Tyr Pro Asp Ala Asn Leu Leu Asn Asp Arg Val Leu Arg Ala Met Leu
            20                  25                  30

Lys Ala Glu Glu Thr Cys Ala Pro Ser Val Ser Tyr Phe Lys Cys Val
        35                  40                  45

Gln Lys Glu Val Leu Pro Ser Met Arg Lys Ile Val Ala Thr Trp Met
    50                  55                  60

Leu Glu Val Cys Glu Glu Gln Lys Cys Glu Glu Val Phe Pro Leu
65                  70                  75                  80

Ala Met Asn Tyr Leu Asp Arg Phe Leu Ser Leu Glu Pro Val Lys Lys
            85                  90                  95

Ser Arg Leu Gln Leu Leu Gly Ala Thr Cys Met Phe Val Ala Ser Lys
        100                 105                 110

Met Lys Glu Thr Ile Pro Leu Thr Ala Glu Lys Leu Cys Ile Tyr Thr
    115                 120                 125

Asp Asn Ser Ile Arg Pro Glu Glu Leu Leu Gln Met Glu Leu Leu Leu
130                 135                 140

Val Asn Lys Leu Lys Trp Asn Leu Ala Ala Met Thr Pro His Asp Phe
145                 150                 155                 160

Ile Glu His Phe Leu Ser Lys Met Pro Glu Ala Glu Glu Asn Lys Gln
            165                 170                 175

Ile Ile Arg Lys His Ala Gln Thr Phe Val Ala Leu Cys Ala Thr Asp
        180                 185                 190

Val Lys Phe Ile Ser Asn Pro Pro Ser Met Val Ala Ala Gly Ser Val
    195                 200                 205

Val Ala Ala Val Gln Gly Leu Asn Leu Arg Ser Pro Asn Asn Phe Leu
210                 215                 220

Ser Tyr Tyr Arg Leu Thr Arg Phe Leu Ser Arg Val Ile Lys Cys Asp
225                 230                 235                 240

Pro Asp Cys Leu Arg Ala Cys Gln Glu Gln Ile Glu Ala Leu Leu Glu
            245                 250                 255

Ser Ser Leu Arg Gln Ala Gln Gln Asn Met Asp Pro Lys Ala Ala Glu
        260                 265                 270

Glu Glu Glu Glu Glu Glu Glu Val Asp Leu Ala Cys Thr Pro Thr
    275                 280                 285

Asp Val Arg Asp Val Asp Ile
290                 295
```

<210> SEQ ID NO 2
<211> LENGTH: 536
<212> TYPE: PRT
<213> ORGANISM: Homo sapiens

<400> SEQUENCE: 2

```
Met Gly Ser Asn Lys Ser Lys Pro Lys Asp Ala Ser Gln Arg Arg Arg
1               5                   10                  15

Ser Leu Glu Pro Ala Glu Asn Val His Gly Ala Gly Gly Gly Ala Phe
            20                  25                  30

Pro Ala Ser Gln Thr Pro Ser Lys Pro Ala Ser Ala Asp Gly His Arg
        35                  40                  45

Gly Pro Ser Ala Ala Phe Ala Pro Ala Ala Ala Glu Pro Lys Leu Phe
    50                  55                  60
```

```
Gly Gly Phe Asn Ser Ser Asp Thr Val Thr Ser Pro Gln Arg Ala Gly
 65                  70                  75                  80

Pro Leu Ala Gly Gly Val Thr Thr Phe Val Ala Leu Tyr Asp Tyr Glu
                 85                  90                  95

Ser Arg Thr Glu Thr Asp Leu Ser Phe Lys Lys Gly Glu Arg Leu Gln
            100                 105                 110

Ile Val Asn Asn Thr Glu Gly Asp Trp Trp Leu Ala His Ser Leu Ser
        115                 120                 125

Thr Gly Gln Thr Gly Tyr Ile Pro Ser Asn Tyr Val Ala Pro Ser Asp
    130                 135                 140

Ser Ile Gln Ala Glu Glu Trp Tyr Phe Gly Lys Ile Thr Arg Arg Glu
145                 150                 155                 160

Ser Glu Arg Leu Leu Leu Asn Ala Glu Asn Pro Arg Gly Thr Phe Leu
                165                 170                 175

Val Arg Glu Ser Glu Thr Thr Lys Gly Ala Tyr Cys Leu Ser Val Ser
            180                 185                 190

Asp Phe Asp Asn Ala Lys Gly Leu Asn Val Lys His Tyr Lys Ile Arg
        195                 200                 205

Lys Leu Asp Ser Gly Gly Phe Tyr Ile Thr Ser Arg Thr Gln Phe Asn
    210                 215                 220

Ser Leu Gln Gln Leu Val Ala Tyr Tyr Ser Lys His Ala Asp Gly Leu
225                 230                 235                 240

Cys His Arg Leu Thr Thr Val Cys Pro Thr Ser Lys Pro Gln Thr Gln
                245                 250                 255

Gly Leu Ala Lys Asp Ala Trp Glu Ile Pro Arg Glu Ser Leu Arg Leu
            260                 265                 270

Glu Val Lys Leu Gly Gln Gly Cys Phe Gly Glu Val Trp Met Gly Thr
        275                 280                 285

Trp Asn Gly Thr Thr Arg Val Ala Ile Lys Thr Leu Lys Pro Gly Thr
    290                 295                 300

Met Ser Pro Glu Ala Phe Leu Gln Glu Ala Gln Val Met Lys Lys Leu
305                 310                 315                 320

Arg His Glu Lys Leu Val Gln Leu Tyr Ala Val Val Ser Glu Glu Pro
                325                 330                 335

Ile Tyr Ile Val Thr Glu Tyr Met Ser Lys Gly Ser Leu Leu Asp Phe
            340                 345                 350

Leu Lys Gly Glu Thr Gly Lys Tyr Leu Arg Leu Pro Gln Leu Val Asp
        355                 360                 365

Met Ala Ala Gln Ile Ala Ser Gly Met Ala Tyr Val Glu Arg Met Asn
    370                 375                 380

Tyr Val His Arg Asp Leu Arg Ala Ala Asn Ile Leu Val Gly Glu Asn
385                 390                 395                 400

Leu Val Cys Lys Val Ala Asp Phe Gly Leu Ala Arg Leu Ile Glu Asp
                405                 410                 415

Asn Glu Tyr Thr Ala Arg Gln Gly Ala Lys Phe Pro Ile Lys Trp Thr
            420                 425                 430

Ala Pro Glu Ala Ala Leu Tyr Gly Arg Phe Thr Ile Lys Ser Asp Val
        435                 440                 445

Trp Ser Phe Gly Ile Leu Leu Thr Glu Leu Thr Lys Gly Arg Val
    450                 455                 460

Pro Tyr Pro Gly Met Val Asn Arg Glu Val Leu Asp Gln Val Glu Arg
465                 470                 475                 480

Gly Tyr Arg Met Pro Cys Pro Pro Glu Cys Pro Glu Ser Leu His Asp
```

```
                    485                 490                 495
Leu Met Cys Gln Cys Trp Arg Lys Glu Pro Glu Glu Arg Pro Thr Phe
            500                 505                 510

Glu Tyr Leu Gln Ala Phe Leu Glu Asp Tyr Phe Thr Ser Thr Glu Pro
            515                 520                 525

Gln Tyr Gln Pro Gly Glu Asn Leu
            530                 535

<210> SEQ ID NO 3
<211> LENGTH: 707
<212> TYPE: PRT
<213> ORGANISM: Homo sapiens

<400> SEQUENCE: 3

Met Ser Leu Trp Gln Pro Leu Val Leu Val Leu Leu Val Leu Gly Cys
1               5                   10                  15

Cys Phe Ala Ala Pro Arg Gln Arg Gln Ser Thr Leu Val Leu Phe Pro
            20                  25                  30

Gly Asp Leu Arg Thr Asn Leu Thr Asp Arg Gln Leu Ala Glu Glu Tyr
        35                  40                  45

Leu Tyr Arg Tyr Gly Tyr Thr Arg Val Ala Glu Met Arg Gly Glu Ser
50                  55                  60

Lys Ser Leu Gly Pro Ala Leu Leu Leu Leu Gln Lys Gln Leu Ser Leu
65                  70                  75                  80

Pro Glu Thr Gly Glu Leu Asp Ser Ala Thr Leu Lys Ala Met Arg Thr
                85                  90                  95

Pro Arg Cys Gly Val Pro Asp Leu Gly Arg Phe Gln Thr Phe Glu Gly
            100                 105                 110

Asp Leu Lys Trp His His His Asn Ile Thr Tyr Trp Ile Gln Asn Tyr
        115                 120                 125

Ser Glu Asp Leu Pro Arg Ala Val Ile Asp Asp Ala Phe Ala Arg Ala
130                 135                 140

Phe Ala Leu Trp Ser Ala Val Thr Pro Leu Thr Phe Thr Arg Val Tyr
145                 150                 155                 160

Ser Arg Asp Ala Asp Ile Val Ile Gln Phe Gly Val Ala Glu His Gly
                165                 170                 175

Asp Gly Tyr Pro Phe Asp Gly Lys Asp Gly Leu Leu Ala His Ala Phe
            180                 185                 190

Pro Pro Gly Pro Gly Ile Gln Gly Asp Ala His Phe Asp Asp Asp Glu
        195                 200                 205

Leu Trp Ser Leu Gly Lys Gly Val Val Val Pro Thr Arg Phe Gly Asn
210                 215                 220

Ala Asp Gly Ala Ala Cys His Phe Pro Phe Ile Phe Glu Gly Arg Ser
225                 230                 235                 240

Tyr Ser Ala Cys Thr Thr Asp Gly Arg Ser Asp Gly Leu Pro Trp Cys
                245                 250                 255

Ser Thr Thr Ala Asn Tyr Asp Thr Asp Asp Arg Phe Gly Phe Cys Pro
            260                 265                 270

Ser Glu Arg Leu Tyr Thr Gln Asp Gly Asn Ala Asp Gly Lys Pro Cys
        275                 280                 285

Gln Phe Pro Phe Ile Phe Gln Gly Gln Ser Tyr Ser Ala Cys Thr Thr
    290                 295                 300

Asp Gly Arg Ser Asp Gly Tyr Arg Trp Cys Ala Thr Thr Ala Asn Tyr
305                 310                 315                 320
```

-continued

```
Asp Arg Asp Lys Leu Phe Gly Phe Cys Pro Thr Arg Ala Asp Ser Thr
                325                 330                 335

Val Met Gly Gly Asn Ser Ala Gly Glu Leu Cys Val Phe Pro Phe Thr
            340                 345                 350

Phe Leu Gly Lys Glu Tyr Ser Thr Cys Thr Ser Glu Gly Arg Gly Asp
        355                 360                 365

Gly Arg Leu Trp Cys Ala Thr Thr Ser Asn Phe Asp Ser Asp Lys Lys
    370                 375                 380

Trp Gly Phe Cys Pro Asp Gln Gly Tyr Ser Leu Phe Leu Val Ala Ala
385                 390                 395                 400

His Glu Phe Gly His Ala Leu Gly Leu Asp His Ser Ser Val Pro Glu
                405                 410                 415

Ala Leu Met Tyr Pro Met Tyr Arg Phe Thr Glu Gly Pro Pro Leu His
            420                 425                 430

Lys Asp Asp Val Asn Gly Ile Arg His Leu Tyr Gly Pro Arg Pro Glu
        435                 440                 445

Pro Glu Pro Arg Pro Pro Thr Thr Thr Pro Gln Pro Thr Ala Pro
    450                 455                 460

Pro Thr Val Cys Pro Thr Gly Pro Pro Thr Val His Pro Ser Glu Arg
465                 470                 475                 480

Pro Thr Ala Gly Pro Thr Gly Pro Ser Ala Gly Pro Thr Gly Pro
                485                 490                 495

Pro Thr Ala Gly Pro Ser Thr Ala Thr Val Pro Leu Ser Pro Val
            500                 505                 510

Asp Asp Ala Cys Asn Val Asn Ile Phe Asp Ala Ile Ala Glu Ile Gly
        515                 520                 525

Asn Gln Leu Tyr Leu Phe Lys Asp Gly Lys Tyr Trp Arg Phe Ser Glu
    530                 535                 540

Gly Arg Gly Ser Arg Pro Gln Gly Pro Phe Leu Ile Ala Asp Lys Trp
545                 550                 555                 560

Pro Ala Leu Pro Arg Lys Leu Asp Ser Val Phe Glu Glu Arg Leu Ser
                565                 570                 575

Lys Lys Leu Phe Phe Phe Ser Gly Arg Gln Val Trp Val Tyr Thr Gly
            580                 585                 590

Ala Ser Val Leu Gly Pro Arg Arg Leu Asp Lys Leu Gly Leu Gly Ala
        595                 600                 605

Asp Val Ala Gln Val Thr Gly Ala Leu Arg Ser Gly Arg Gly Lys Met
    610                 615                 620

Leu Leu Phe Ser Gly Arg Arg Leu Trp Arg Phe Asp Val Lys Ala Gln
625                 630                 635                 640

Met Val Asp Pro Arg Ser Ala Ser Glu Val Asp Arg Met Phe Pro Gly
                645                 650                 655

Val Pro Leu Asp Thr His Asp Val Phe Gln Tyr Arg Glu Lys Ala Tyr
            660                 665                 670

Phe Cys Gln Asp Arg Phe Tyr Trp Arg Val Ser Ser Arg Ser Glu Leu
        675                 680                 685

Asn Gln Val Asp Gln Val Gly Tyr Val Thr Tyr Asp Ile Leu Gln Cys
    690                 695                 700

Pro Glu Asp
705

<210> SEQ ID NO 4
<211> LENGTH: 345
<212> TYPE: PRT
```

<213> ORGANISM: Homo sapiens

<400> SEQUENCE: 4

Met Pro Ala Arg Ala Leu Leu Pro Arg Arg Met Gly His Arg Thr Leu
1               5                   10                  15
Ala Ser Thr Pro Ala Leu Trp Ala Ser Ile Pro Cys Pro Arg Ser Glu
            20                  25                  30
Leu Arg Leu Asp Leu Val Leu Pro Ser Gly Gln Ser Phe Arg Trp Arg
        35                  40                  45
Glu Gln Ser Pro Ala His Trp Ser Gly Val Leu Ala Asp Gln Val Trp
    50                  55                  60
Thr Leu Thr Gln Thr Glu Glu Gln Leu His Cys Thr Val Tyr Arg Gly
65                  70                  75                  80
Asp Lys Ser Gln Ala Ser Arg Pro Thr Pro Asp Glu Leu Glu Ala Val
                85                  90                  95
Arg Lys Tyr Phe Gln Leu Asp Val Thr Leu Ala Gln Leu Tyr His His
            100                 105                 110
Trp Gly Ser Val Asp Ser His Phe Gln Glu Val Ala Gln Lys Phe Gln
        115                 120                 125
Gly Val Arg Leu Leu Arg Gln Asp Pro Ile Glu Cys Leu Phe Ser Phe
    130                 135                 140
Ile Cys Ser Ser Asn Asn Asn Ile Ala Arg Ile Thr Gly Met Val Glu
145                 150                 155                 160
Arg Leu Cys Gln Ala Phe Gly Pro Arg Leu Ile Gln Leu Asp Asp Val
                165                 170                 175
Thr Tyr His Gly Phe Pro Ser Leu Gln Ala Leu Ala Gly Pro Glu Val
            180                 185                 190
Glu Ala His Leu Arg Lys Leu Gly Leu Gly Tyr Arg Ala Arg Tyr Val
        195                 200                 205
Ser Ala Ser Ala Arg Ala Ile Leu Glu Glu Gln Gly Gly Leu Ala Trp
    210                 215                 220
Leu Gln Gln Leu Arg Glu Ser Ser Tyr Glu Glu Ala His Lys Ala Leu
225                 230                 235                 240
Cys Ile Leu Pro Gly Val Gly Thr Lys Val Ala Asp Cys Ile Cys Leu
                245                 250                 255
Met Ala Leu Asp Lys Pro Gln Ala Val Pro Val Asp Val His Met Trp
            260                 265                 270
His Ile Ala Gln Arg Asp Tyr Ser Trp His Pro Thr Thr Ser Gln Ala
        275                 280                 285
Lys Gly Pro Ser Pro Gln Thr Asn Lys Glu Leu Gly Asn Phe Phe Arg
    290                 295                 300
Ser Leu Trp Gly Pro Tyr Ala Gly Trp Ala Gln Ala Val Leu Phe Ser
305                 310                 315                 320
Ala Asp Leu Arg Gln Ser Arg His Ala Gln Glu Pro Pro Ala Lys Arg
                325                 330                 335
Arg Lys Gly Ser Lys Gly Pro Glu Gly
            340                 345

<210> SEQ ID NO 5
<211> LENGTH: 324
<212> TYPE: PRT
<213> ORGANISM: Homo sapiens

<400> SEQUENCE: 5

Met Pro Ala Arg Ala Leu Leu Pro Arg Arg Met Gly His Arg Thr Leu

```
                1               5                   10                  15
            Ala Ser Thr Pro Ala Leu Trp Ala Ser Ile Pro Cys Pro Arg Ser Glu
                        20                  25                  30

Leu Arg Leu Asp Leu Val Leu Pro Ser Gly Gln Ser Phe Arg Trp Arg
                        35                  40                  45

Glu Gln Ser Pro Ala His Trp Ser Gly Val Leu Ala Asp Gln Val Trp
                        50                  55                  60

Thr Leu Thr Gln Thr Glu Gln Leu His Cys Thr Val Tyr Arg Gly
            65                  70                  75                  80

Asp Lys Ser Gln Ala Ser Arg Pro Thr Pro Asp Glu Leu Glu Ala Val
                        85                  90                  95

Arg Lys Tyr Phe Gln Leu Asp Val Thr Leu Ala Gln Leu Tyr His His
                        100                 105                 110

Trp Gly Ser Val Asp Ser His Phe Gln Glu Val Ala Gln Lys Phe Gln
                        115                 120                 125

Gly Val Arg Leu Leu Arg Gln Asp Pro Ile Glu Cys Leu Phe Ser Phe
                        130                 135                 140

Ile Cys Ser Ser Asn Asn Asn Ile Ala Arg Ile Thr Gly Met Val Glu
            145                 150                 155                 160

Arg Leu Cys Gln Ala Phe Gly Pro Arg Leu Ile Gln Leu Asp Asp Val
                        165                 170                 175

Thr Tyr His Gly Phe Pro Ser Leu Gln Ala Leu Ala Gly Pro Glu Val
                        180                 185                 190

Glu Ala His Leu Arg Lys Leu Gly Leu Gly Tyr Arg Ala Arg Tyr Val
                        195                 200                 205

Ser Ala Ser Ala Arg Ala Ile Leu Glu Glu Gln Gly Gly Leu Ala Trp
                        210                 215                 220

Leu Gln Gln Leu Arg Glu Ser Ser Tyr Glu Glu Ala His Lys Ala Leu
            225                 230                 235                 240

Cys Ile Leu Pro Gly Val Gly Thr Lys Val Ala Asp Cys Ile Cys Leu
                        245                 250                 255

Met Ala Leu Asp Lys Pro Gln Ala Val Pro Val Asp Val His Met Trp
                        260                 265                 270

His Ile Ala Gln Arg Asp Tyr Ser Trp His Pro Thr Thr Ser Gln Ala
                        275                 280                 285

Lys Gly Pro Ser Pro Gln Thr Asn Lys Glu Leu Gly Asn Phe Phe Arg
                        290                 295                 300

Ser Leu Trp Gly Pro Tyr Ala Gly Trp Ala Gln Ala Val Ser Val Pro
            305                 310                 315                 320

Arg Cys Pro Pro

<210> SEQ ID NO 6
<211> LENGTH: 410
<212> TYPE: PRT
<213> ORGANISM: Homo sapiens

<400> SEQUENCE: 6

Met Pro Ala Arg Ala Leu Leu Pro Arg Arg Met Gly His Arg Thr Leu
            1               5                   10                  15

Ala Ser Thr Pro Ala Leu Trp Ala Ser Ile Pro Cys Pro Arg Ser Glu
                        20                  25                  30

Leu Arg Leu Asp Leu Val Leu Pro Ser Gly Gln Ser Phe Arg Trp Arg
                        35                  40                  45

Glu Gln Ser Pro Ala His Trp Ser Gly Val Leu Ala Asp Gln Val Trp
```

```
Thr Leu Thr Gln Thr Glu Glu Gln Leu His Cys Thr Val Tyr Arg Gly
 65                  70                  75                  80

Asp Lys Ser Gln Ala Ser Arg Pro Thr Pro Asp Leu Glu Ala Val
                 85                  90                  95

Arg Lys Tyr Phe Gln Leu Asp Val Thr Leu Ala Gln Leu Tyr His His
            100                 105                 110

Trp Gly Ser Val Asp Ser His Phe Gln Glu Val Ala Gln Lys Phe Gln
        115                 120                 125

Gly Val Arg Leu Leu Arg Gln Asp Pro Ile Glu Cys Leu Phe Ser Phe
130                 135                 140

Ile Cys Ser Ser Asn Asn Asn Ile Ala Arg Ile Thr Gly Met Val Glu
145                 150                 155                 160

Arg Leu Cys Gln Ala Phe Gly Pro Arg Leu Ile Gln Leu Asp Asp Val
                165                 170                 175

Thr Tyr His Gly Phe Pro Ser Leu Gln Ala Leu Ala Gly Pro Glu Val
            180                 185                 190

Glu Ala His Leu Arg Lys Leu Gly Leu Gly Tyr Arg Ala Arg Tyr Val
        195                 200                 205

Ser Ala Ser Ala Arg Ala Ile Leu Glu Glu Gln Gly Gly Leu Ala Trp
210                 215                 220

Leu Gln Gln Leu Arg Glu Ser Ser Tyr Glu Glu Ala His Lys Ala Leu
225                 230                 235                 240

Cys Ile Leu Pro Gly Val Gly Thr Lys Val Ala Asp Cys Ile Cys Leu
                245                 250                 255

Met Ala Leu Asp Lys Pro Gln Ala Val Pro Val Asp Val His Met Trp
            260                 265                 270

His Ile Ala Gln Arg Asp Tyr Ser Trp His Pro Thr Thr Ser Gln Ala
        275                 280                 285

Lys Gly Pro Ser Pro Gln Thr Asn Lys Glu Leu Gly Asn Phe Phe Arg
290                 295                 300

Ser Leu Trp Gly Pro Tyr Ala Gly Trp Ala Gln Ala Thr Pro Pro Ser
305                 310                 315                 320

Tyr Arg Cys Cys Ser Val Pro Thr Cys Ala Asn Pro Ala Met Leu Arg
                325                 330                 335

Ser His Gln Gln Ser Ala Glu Arg Val Pro Lys Gly Arg Lys Ala Arg
            340                 345                 350

Trp Gly Thr Leu Asp Lys Glu Ile Pro Gln Ala Pro Ser Pro Pro Phe
        355                 360                 365

Pro Thr Ser Leu Ser Pro Ser Pro Ser Leu Met Leu Gly Arg Gly
370                 375                 380

Leu Pro Val Thr Thr Ser Lys Ala Arg His Pro Gln Ile Lys Gln Ser
385                 390                 395                 400

Val Cys Thr Thr Arg Trp Gly Gly Gly Tyr
                405                 410

<210> SEQ ID NO 7
<211> LENGTH: 424
<212> TYPE: PRT
<213> ORGANISM: Homo sapiens

<400> SEQUENCE: 7

Met Pro Ala Arg Ala Leu Leu Pro Arg Arg Met Gly His Arg Thr Leu
 1               5                  10                  15
```

-continued

```
Ala Ser Thr Pro Ala Leu Trp Ala Ser Ile Pro Cys Pro Arg Ser Glu
            20                  25                  30

Leu Arg Leu Asp Leu Val Leu Pro Ser Gly Gln Ser Phe Arg Trp Arg
        35                  40                  45

Glu Gln Ser Pro Ala His Trp Ser Gly Val Leu Ala Asp Gln Val Trp
    50                  55                  60

Thr Leu Thr Gln Thr Glu Gln Leu His Cys Thr Val Tyr Arg Gly
65                  70                  75                  80

Asp Lys Ser Gln Ala Ser Arg Pro Thr Pro Asp Glu Leu Glu Ala Val
            85                  90                  95

Arg Lys Tyr Phe Gln Leu Asp Val Thr Leu Ala Gln Leu Tyr His His
        100                 105                 110

Trp Gly Ser Val Asp Ser His Phe Gln Glu Val Ala Gln Lys Phe Gln
    115                 120                 125

Gly Val Arg Leu Leu Arg Gln Asp Pro Ile Glu Cys Leu Phe Ser Phe
    130                 135                 140

Ile Cys Ser Ser Asn Asn Asn Ile Ala Arg Ile Thr Gly Met Val Glu
145                 150                 155                 160

Arg Leu Cys Gln Ala Phe Gly Pro Arg Leu Ile Gln Leu Asp Asp Val
            165                 170                 175

Thr Tyr His Gly Phe Pro Ser Leu Gln Ala Leu Ala Gly Pro Glu Val
        180                 185                 190

Glu Ala His Leu Arg Lys Leu Gly Leu Gly Tyr Arg Ala Arg Tyr Val
    195                 200                 205

Ser Ala Ser Ala Arg Ala Ile Leu Glu Glu Gln Gly Gly Leu Ala Trp
    210                 215                 220

Leu Gln Gln Leu Arg Glu Ser Ser Tyr Glu Glu Ala His Lys Ala Leu
225                 230                 235                 240

Cys Ile Leu Pro Gly Val Gly Thr Lys Val Ala Asp Cys Ile Cys Leu
            245                 250                 255

Met Ala Leu Asp Lys Pro Gln Ala Val Pro Val Asp Val His Met Trp
        260                 265                 270

His Ile Ala Gln Arg Asp Tyr Ser Trp His Pro Thr Thr Ser Gln Ala
    275                 280                 285

Lys Gly Pro Ser Pro Gln Thr Asn Lys Glu Leu Gly Asn Phe Phe Arg
    290                 295                 300

Ser Leu Trp Gly Pro Tyr Ala Gly Trp Ala Gln Ala Gly Leu Leu Gly
305                 310                 315                 320

Asn Ala Phe Asp Gly His Gln Leu Leu Arg Pro Leu Ile Phe Cys Gln
            325                 330                 335

Asp His Leu Arg Glu Gly Pro Ile Gly Arg Gly Asp Ser Gln Gly
        340                 345                 350

Glu Glu Leu Glu Pro Gln Leu Pro Ser Ser Leu Ser Ser Ile Pro Tyr
    355                 360                 365

Gly Phe Cys Asp His Cys Trp Thr Lys Asp Val Asp Asp Pro Pro Leu
    370                 375                 380

Val Thr His Pro Ser Pro Gly Ser Arg Asp Gly His Met Thr Gln Ala
385                 390                 395                 400

Trp Pro Val Lys Val Val Ser Pro Leu Ala Thr Val Ile Gly His Val
            405                 410                 415

Met Gln Ala Ser Leu Leu Ala Leu
        420
```

-continued

```
<210> SEQ ID NO 8
<211> LENGTH: 357
<212> TYPE: PRT
<213> ORGANISM: Homo sapiens

<400> SEQUENCE: 8
```

Met Pro Ala Arg Ala Leu Leu Pro Arg Arg Met Gly His Arg Thr Leu
1               5                   10                  15

Ala Ser Thr Pro Ala Leu Trp Ala Ser Ile Pro Cys Pro Arg Ser Glu
            20                  25                  30

Leu Arg Leu Asp Leu Val Leu Pro Ser Gly Gln Ser Phe Arg Trp Arg
        35                  40                  45

Glu Gln Ser Pro Ala His Trp Ser Gly Val Leu Ala Asp Gln Val Trp
50                  55                  60

Thr Leu Thr Gln Thr Glu Glu Gln Leu His Cys Thr Val Tyr Arg Gly
65                  70                  75                  80

Asp Lys Ser Gln Ala Ser Arg Pro Thr Pro Asp Glu Leu Glu Ala Val
                85                  90                  95

Arg Lys Tyr Phe Gln Leu Asp Val Thr Leu Ala Gln Leu Tyr His His
            100                 105                 110

Trp Gly Ser Val Asp Ser His Phe Gln Glu Val Ala Gln Lys Phe Gln
        115                 120                 125

Gly Val Arg Leu Leu Arg Gln Asp Pro Ile Glu Cys Leu Phe Ser Phe
130                 135                 140

Ile Cys Ser Ser Asn Asn Asn Ile Ala Arg Ile Thr Gly Met Val Glu
145                 150                 155                 160

Arg Leu Cys Gln Ala Phe Gly Pro Arg Leu Ile Gln Leu Asp Asp Val
                165                 170                 175

Thr Tyr His Gly Phe Pro Ser Leu Gln Ala Leu Ala Gly Pro Glu Val
            180                 185                 190

Glu Ala His Leu Arg Lys Leu Gly Leu Gly Tyr Arg Ala Arg Tyr Val
        195                 200                 205

Ser Ala Ser Ala Arg Ala Ile Leu Glu Glu Gln Gly Gly Leu Ala Trp
210                 215                 220

Leu Gln Gln Leu Arg Glu Ser Ser Tyr Glu Glu Ala His Lys Ala Leu
225                 230                 235                 240

Cys Ile Leu Pro Gly Val Gly Thr Lys Gly Leu Leu Gly Asn Ala Phe
                245                 250                 255

Asp Gly His Gln Leu Leu Arg Pro Leu Ile Phe Cys Gln Asp His Leu
            260                 265                 270

Arg Glu Gly Pro Pro Ile Gly Arg Gly Asp Ser Gln Gly Glu Glu Leu
        275                 280                 285

Glu Pro Gln Leu Pro Ser Ser Leu Ser Ser Ile Pro Tyr Gly Phe Cys
290                 295                 300

Asp His Cys Trp Thr Lys Asp Val Asp Pro Pro Leu Val Thr His Pro
305                 310                 315                 320

Pro Ser Pro Gly Ser Arg Asp Gly His Met Thr Gln Ala Trp Pro Val
                325                 330                 335

Lys Val Val Ser Pro Leu Ala Thr Val Ile Gly His Val Met Gln Ala
            340                 345                 350

Ser Leu Leu Ala Leu
        355

```
<210> SEQ ID NO 9
<211> LENGTH: 195
```

<212> TYPE: PRT
<213> ORGANISM: Homo sapiens

<400> SEQUENCE: 9

```
Met Pro Ala Arg Ala Leu Leu Pro Arg Arg Met Gly His Arg Thr Leu
1               5                   10                  15

Ala Ser Thr Pro Ala Leu Trp Ala Ser Ile Pro Cys Pro Arg Ser Glu
            20                  25                  30

Leu Arg Leu Asp Leu Val Leu Pro Ser Gly Gln Ser Phe Arg Trp Arg
        35                  40                  45

Glu Gln Ser Pro Ala His Trp Ser Gly Val Leu Ala Asp Gln Val Trp
    50                  55                  60

Thr Leu Thr Gln Thr Glu Glu Gln Leu His Cys Thr Val Tyr Arg Gly
65                  70                  75                  80

Asp Lys Ser Gln Ala Ser Arg Pro Thr Pro Asp Glu Leu Glu Ala Val
                85                  90                  95

Arg Lys Tyr Phe Gln Leu Asp Val Thr Leu Ala Gln Leu Tyr His His
            100                 105                 110

Trp Gly Ser Val Asp Ser His Phe Gln Glu Val Ala Gln Lys Phe Gln
        115                 120                 125

Gly Val Arg Leu Leu Arg Gln Asp Pro Ile Glu Cys Leu Phe Ser Phe
    130                 135                 140

Ile Cys Ser Ser Asn Asn Asn Ile Ala Arg Ile Thr Gly Met Val Glu
145                 150                 155                 160

Arg Leu Cys Gln Ala Phe Gly Pro Arg Leu Ile Gln Leu Asp Asp Val
                165                 170                 175

Thr Tyr His Gly Phe Pro Ser Leu Gln Ala Leu Ala Gly Pro Pro Trp
            180                 185                 190

Gln Cys Ile
        195
```

<210> SEQ ID NO 10
<211> LENGTH: 356
<212> TYPE: PRT
<213> ORGANISM: Homo sapiens

<400> SEQUENCE: 10

```
Met Pro Ala Arg Ala Leu Leu Pro Arg Arg Met Gly His Arg Thr Leu
1               5                   10                  15

Ala Ser Thr Pro Ala Leu Trp Ala Ser Ile Pro Cys Pro Arg Ser Glu
            20                  25                  30

Leu Arg Leu Asp Leu Val Leu Pro Ser Gly Gln Ser Phe Arg Trp Arg
        35                  40                  45

Glu Gln Ser Pro Ala His Trp Ser Gly Val Leu Ala Asp Gln Val Trp
    50                  55                  60

Thr Leu Thr Gln Thr Glu Glu Gln Leu His Cys Thr Val Tyr Arg Gly
65                  70                  75                  80

Asp Lys Ser Gln Ala Ser Arg Pro Thr Pro Asp Glu Leu Glu Ala Val
                85                  90                  95

Arg Lys Tyr Phe Gln Leu Asp Val Thr Leu Ala Gln Leu Tyr His His
            100                 105                 110

Trp Gly Ser Val Asp Ser His Phe Gln Glu Val Ala Gln Lys Phe Gln
        115                 120                 125

Gly Val Arg Leu Leu Arg Gln Asp Pro Ile Glu Cys Leu Phe Ser Phe
    130                 135                 140
```

-continued

```
Ile Cys Ser Ser Asn Asn Asn Ile Ala Arg Ile Thr Gly Met Val Glu
145                 150                 155                 160

Arg Leu Cys Gln Ala Phe Gly Pro Arg Leu Ile Gln Leu Asp Asp Val
                165                 170                 175

Thr Tyr His Gly Phe Pro Ser Leu Gln Ala Leu Ala Gly Pro Glu Val
            180                 185                 190

Glu Ala His Leu Arg Lys Leu Gly Leu Gly Tyr Arg Ala Arg Tyr Val
        195                 200                 205

Ser Ala Ser Ala Arg Ala Ile Leu Glu Glu Gln Gly Gly Leu Ala Trp
    210                 215                 220

Leu Gln Gln Leu Arg Glu Ser Ser Tyr Glu Glu Ala His Lys Ala Leu
225                 230                 235                 240

Cys Ile Leu Pro Gly Val Gly Thr Lys Val Ala Asp Cys Ile Cys Leu
                245                 250                 255

Met Ala Leu Asp Lys Pro Gln Ala Val Pro Val Asp Val His Met Trp
            260                 265                 270

His Ile Ala Gln Arg Asp Tyr Ser Trp His Pro Thr Thr Ser Gln Ala
        275                 280                 285

Lys Gly Pro Ser Pro Gln Thr Asn Lys Glu Leu Gly Asn Phe Phe Arg
    290                 295                 300

Ser Leu Trp Gly Pro Tyr Ala Gly Trp Ala Gln Ala Leu Cys Gln Val
305                 310                 315                 320

Ile Thr Thr Phe Met Thr Phe Leu Gly Pro His Arg Leu Asp Gln Met
                325                 330                 335

Pro Pro Glu Glu Leu Gln Thr Ser Ser Ser Arg Leu Gly Gly Pro Pro
            340                 345                 350

Trp Gln Cys Ile
        355

<210> SEQ ID NO 11
<211> LENGTH: 322
<212> TYPE: PRT
<213> ORGANISM: Homo sapiens

<400> SEQUENCE: 11

Met Pro Ala Arg Ala Leu Leu Pro Arg Arg Met Gly His Arg Thr Leu
1               5                   10                  15

Ala Ser Thr Pro Ala Leu Trp Ala Ser Ile Pro Cys Pro Arg Ser Glu
                20                  25                  30

Leu Arg Leu Asp Leu Val Leu Pro Ser Gly Gln Ser Phe Arg Trp Arg
            35                  40                  45

Glu Gln Ser Pro Ala His Trp Ser Gly Val Leu Ala Asp Gln Val Trp
        50                  55                  60

Thr Leu Thr Gln Thr Glu Gln Leu His Cys Thr Val Tyr Arg Gly Asp
65                  70                  75                  80

Asp Lys Ser Gln Ala Ser Arg Pro Thr Pro Asp Glu Leu Glu Ala Val
                85                  90                  95

Arg Lys Tyr Phe Gln Leu Asp Val Thr Leu Ala Gln Leu Tyr His His
            100                 105                 110

Trp Gly Ser Val Asp Ser His Phe Gln Glu Val Ala Gln Lys Phe Gln
        115                 120                 125

Gly Val Arg Leu Leu Arg Gln Asp Pro Ile Glu Cys Leu Phe Ser Phe
    130                 135                 140

Ile Cys Ser Ser Asn Asn Asn Ile Ala Arg Ile Thr Gly Met Val Glu
145                 150                 155                 160
```

```
Arg Leu Cys Gln Ala Phe Gly Pro Arg Leu Ile Gln Leu Asp Asp Val
                165                 170                 175

Thr Tyr His Gly Phe Pro Ser Leu Gln Ala Leu Ala Gly Pro Glu Val
            180                 185                 190

Glu Ala His Leu Arg Lys Leu Gly Leu Gly Tyr Arg Ala Arg Tyr Val
        195                 200                 205

Ser Ala Ser Ala Arg Ala Ile Leu Glu Glu Gln Gly Gly Leu Ala Trp
    210                 215                 220

Leu Gln Gln Leu Arg Glu Ser Ser Tyr Glu Glu Ala His Lys Ala Leu
225                 230                 235                 240

Cys Ile Leu Pro Gly Val Gly Thr Lys Val Ala Asp Cys Ile Cys Leu
                245                 250                 255

Met Ala Leu Asp Lys Pro Gln Ala Val Pro Val Asp Val His Met Trp
            260                 265                 270

His Ile Ala Gln Arg Asp Tyr Ser Trp His Pro Thr Thr Ser Gln Ala
        275                 280                 285

Lys Gly Pro Ser Pro Gln Thr Asn Lys Glu Leu Gly Asn Phe Phe Arg
    290                 295                 300

Ser Leu Trp Gly Pro Tyr Ala Gly Trp Ala Gln Ala Ala Gly Ser Asp
305                 310                 315                 320

Ala Ser

<210> SEQ ID NO 12
<211> LENGTH: 375
<212> TYPE: PRT
<213> ORGANISM: Homo sapiens

<400> SEQUENCE: 12

Met Asp Ala Leu Gln Leu Ala Asn Ser Ala Phe Ala Val Asp Leu Phe
1               5                   10                  15

Lys Gln Leu Cys Glu Lys Glu Pro Leu Gly Asn Val Leu Phe Ser Pro
            20                  25                  30

Ile Cys Leu Ser Thr Ser Leu Ser Leu Ala Gln Val Gly Ala Lys Gly
        35                  40                  45

Asp Thr Ala Asn Glu Ile Gly Gln Val Leu His Phe Glu Asn Val Lys
    50                  55                  60

Asp Val Pro Phe Gly Phe Gln Thr Val Thr Ser Asp Val Asn Lys Leu
65                  70                  75                  80

Ser Ser Phe Tyr Ser Leu Lys Leu Ile Lys Arg Leu Tyr Val Asp Lys
                85                  90                  95

Ser Leu Asn Leu Ser Thr Glu Phe Ile Ser Ser Thr Lys Arg Pro Tyr
            100                 105                 110

Ala Lys Glu Leu Glu Thr Val Asp Phe Lys Asp Lys Leu Glu Glu Thr
        115                 120                 125

Lys Gly Gln Ile Asn Asn Ser Ile Lys Asp Leu Thr Asp Gly His Phe
    130                 135                 140

Glu Asn Ile Leu Ala Asp Asn Ser Val Asn Asp Gln Thr Lys Ile Leu
145                 150                 155                 160

Val Val Asn Ala Ala Tyr Phe Val Gly Lys Trp Met Lys Lys Phe Ser
                165                 170                 175

Glu Ser Glu Thr Lys Glu Cys Pro Phe Arg Val Asn Lys Thr Asp Thr
            180                 185                 190

Lys Pro Val Gln Met Met Asn Met Glu Ala Thr Phe Cys Met Gly Asn
        195                 200                 205
```

```
Ile Asp Ser Ile Asn Cys Lys Ile Ile Glu Leu Pro Phe Gln Asn Lys
    210                 215                 220

His Leu Ser Met Phe Ile Leu Leu Pro Lys Asp Val Glu Asp Glu Ser
225                 230                 235                 240

Thr Gly Leu Glu Lys Ile Glu Lys Gln Leu Asn Ser Glu Ser Leu Ser
                245                 250                 255

Gln Trp Thr Asn Pro Ser Thr Met Ala Asn Ala Lys Val Lys Leu Ser
            260                 265                 270

Ile Pro Lys Phe Lys Val Glu Lys Met Ile Asp Pro Lys Ala Cys Leu
        275                 280                 285

Glu Asn Leu Gly Leu Lys His Ile Phe Ser Glu Asp Thr Ser Asp Phe
290                 295                 300

Ser Gly Met Ser Glu Thr Lys Gly Val Ala Leu Ser Asn Val Ile His
305                 310                 315                 320

Lys Val Cys Leu Glu Ile Thr Glu Asp Gly Gly Asp Ser Ile Glu Val
                325                 330                 335

Pro Gly Ala Arg Ile Leu Gln His Lys Asp Glu Leu Asn Ala Asp His
            340                 345                 350

Pro Phe Ile Tyr Ile Ile Arg His Asn Lys Thr Arg Asn Ile Ile Phe
        355                 360                 365

Phe Gly Lys Phe Cys Ser Pro
370                 375

<210> SEQ ID NO 13
<211> LENGTH: 3256
<212> TYPE: PRT
<213> ORGANISM: Homo sapiens

<400> SEQUENCE: 13

Met Trp Pro Thr Arg Arg Leu Val Thr Ile Lys Arg Ser Gly Val Asp
1               5                   10                  15

Gly Pro His Phe Pro Leu Ser Leu Ser Thr Cys Leu Phe Gly Arg Gly
            20                  25                  30

Ile Glu Cys Asp Ile Arg Ile Gln Leu Pro Val Val Ser Lys Gln His
        35                  40                  45

Cys Lys Ile Glu Ile His Glu Gln Glu Ala Ile Leu His Asn Phe Ser
    50                  55                  60

Ser Thr Asn Pro Thr Gln Val Asn Gly Ser Val Ile Asp Glu Pro Val
65                  70                  75                  80

Arg Leu Lys His Gly Asp Val Ile Thr Ile Ile Asp Arg Ser Phe Arg
                85                  90                  95

Tyr Glu Asn Glu Ser Leu Gln Asn Gly Arg Lys Ser Thr Glu Phe Pro
            100                 105                 110

Arg Lys Ile Arg Glu Gln Glu Pro Ala Arg Arg Val Ser Arg Ser Ser
        115                 120                 125

Phe Ser Ser Asp Pro Asp Glu Lys Ala Gln Asp Ser Lys Ala Tyr Ser
    130                 135                 140

Lys Ile Thr Glu Gly Lys Val Ser Gly Asn Pro Gln Val His Ile Lys
145                 150                 155                 160

Asn Val Lys Glu Asp Ser Thr Ala Asp Asp Ser Lys Asp Ser Val Ala
                165                 170                 175

Gln Gly Thr Thr Asn Val His Ser Ser Glu His Ala Gly Arg Asn Gly
            180                 185                 190

Arg Asn Ala Ala Asp Pro Ile Ser Gly Asp Phe Lys Glu Ile Ser Ser
```

```
            195                 200                 205
Val Lys Leu Val Ser Arg Tyr Gly Glu Leu Lys Ser Val Pro Thr Thr
210                 215                 220

Gln Cys Leu Asp Asn Ser Lys Lys Asn Glu Ser Pro Phe Trp Lys Leu
225                 230                 235                 240

Tyr Glu Ser Val Lys Glu Leu Asp Val Lys Ser Gln Lys Glu Asn
                245                 250                 255

Val Leu Gln Tyr Cys Arg Lys Ser Gly Leu Gln Thr Asp Tyr Ala Thr
                260                 265                 270

Glu Lys Glu Ser Ala Asp Gly Leu Gln Gly Glu Thr Gln Leu Leu Val
                275                 280                 285

Ser Arg Lys Ser Arg Pro Lys Ser Gly Gly Ser Gly His Ala Val Ala
290                 295                 300

Glu Pro Ala Ser Pro Glu Gln Glu Leu Asp Gln Asn Lys Gly Lys Gly
305                 310                 315                 320

Arg Asp Val Glu Ser Val Gln Thr Pro Ser Lys Ala Val Gly Ala Ser
                325                 330                 335

Phe Pro Leu Tyr Glu Pro Ala Lys Met Lys Thr Pro Val Gln Tyr Ser
                340                 345                 350

Gln Gln Gln Asn Ser Pro Gln Lys His Lys Asn Lys Asp Leu Tyr Thr
                355                 360                 365

Thr Gly Arg Arg Glu Ser Val Asn Leu Gly Lys Ser Glu Gly Phe Lys
370                 375                 380

Ala Gly Asp Lys Thr Leu Thr Pro Arg Lys Leu Ser Thr Arg Asn Arg
385                 390                 395                 400

Thr Pro Ala Lys Val Glu Asp Ala Ala Asp Ser Ala Thr Lys Pro Glu
                405                 410                 415

Asn Leu Ser Ser Lys Thr Arg Gly Ser Ile Pro Thr Asp Val Glu Val
                420                 425                 430

Leu Pro Thr Glu Thr Glu Ile His Asn Glu Pro Phe Leu Thr Leu Trp
                435                 440                 445

Leu Thr Gln Val Glu Arg Lys Ile Gln Lys Asp Ser Leu Ser Lys Pro
450                 455                 460

Glu Lys Leu Gly Thr Thr Ala Gly Gln Met Cys Ser Gly Leu Pro Gly
465                 470                 475                 480

Leu Ser Ser Val Asp Ile Asn Asn Phe Gly Asp Ser Ile Asn Glu Ser
                485                 490                 495

Glu Gly Ile Pro Leu Lys Arg Arg Val Ser Phe Gly Gly His Leu
                500                 505                 510

Arg Pro Glu Leu Phe Asp Glu Asn Leu Pro Pro Asn Thr Pro Leu Lys
                515                 520                 525

Arg Gly Glu Ala Pro Thr Lys Arg Lys Ser Leu Val Met His Thr Pro
                530                 535                 540

Pro Val Leu Lys Lys Ile Ile Lys Glu Gln Pro Gln Pro Ser Gly Lys
545                 550                 555                 560

Gln Glu Ser Gly Ser Glu Ile His Val Glu Val Lys Ala Gln Ser Leu
                565                 570                 575

Val Ile Ser Pro Pro Ala Pro Ser Pro Arg Lys Thr Pro Val Ala Ser
                580                 585                 590

Asp Gln Arg Arg Arg Ser Cys Lys Thr Ala Pro Ala Ser Ser Ser Lys
                595                 600                 605

Ser Gln Thr Glu Val Pro Lys Arg Gly Gly Arg Lys Ser Gly Asn Leu
                610                 615                 620
```

```
Pro Ser Lys Arg Val Ser Ile Ser Arg Ser Gln His Asp Ile Leu Gln
625                 630                 635                 640

Met Ile Cys Ser Lys Arg Arg Ser Gly Ala Ser Glu Ala Asn Leu Ile
            645                 650                 655

Val Ala Lys Ser Trp Ala Asp Val Val Lys Leu Gly Ala Lys Gln Thr
                660                 665                 670

Gln Thr Lys Val Ile Lys His Gly Pro Gln Arg Ser Met Asn Lys Arg
            675                 680                 685

Gln Arg Arg Pro Ala Thr Pro Lys Lys Pro Val Gly Glu Val His Ser
690                 695                 700

Gln Phe Ser Thr Gly His Ala Asn Ser Pro Cys Thr Ile Ile Ile Gly
705                 710                 715                 720

Lys Ala His Thr Glu Lys Val His Val Pro Ala Arg Pro Tyr Arg Val
                725                 730                 735

Leu Asn Asn Phe Ile Ser Asn Gln Lys Met Asp Phe Lys Glu Asp Leu
                740                 745                 750

Ser Gly Ile Ala Glu Met Phe Lys Thr Pro Val Lys Glu Gln Pro Gln
            755                 760                 765

Leu Thr Ser Thr Cys His Ile Ala Ile Ser Asn Ser Glu Asn Leu Leu
770                 775                 780

Gly Lys Gln Phe Gln Gly Thr Asp Ser Gly Glu Glu Pro Leu Leu Pro
785                 790                 795                 800

Thr Ser Glu Ser Phe Gly Gly Asn Val Phe Phe Ser Ala Gln Asn Ala
                805                 810                 815

Ala Lys Gln Pro Ser Asp Lys Cys Ser Ala Ser Pro Pro Leu Arg Arg
                820                 825                 830

Gln Cys Ile Arg Glu Asn Gly Asn Val Ala Lys Thr Pro Arg Asn Thr
            835                 840                 845

Tyr Lys Met Thr Ser Leu Glu Thr Lys Thr Ser Asp Thr Glu Thr Glu
850                 855                 860

Pro Ser Lys Thr Val Ser Thr Ala Asn Arg Ser Gly Arg Ser Thr Glu
865                 870                 875                 880

Phe Arg Asn Ile Gln Lys Leu Pro Val Glu Ser Lys Ser Glu Glu Thr
                885                 890                 895

Asn Thr Glu Ile Val Glu Cys Ile Leu Lys Arg Gly Gln Lys Ala Thr
            900                 905                 910

Leu Leu Gln Gln Arg Arg Glu Gly Glu Met Lys Glu Ile Glu Arg Pro
            915                 920                 925

Phe Glu Thr Tyr Lys Glu Asn Ile Glu Leu Lys Glu Asn Asp Glu Lys
            930                 935                 940

Met Lys Ala Met Lys Arg Ser Arg Thr Trp Gly Gln Lys Cys Ala Pro
945                 950                 955                 960

Met Ser Asp Leu Thr Asp Leu Lys Ser Leu Pro Asp Thr Glu Leu Met
                965                 970                 975

Lys Asp Thr Ala Arg Gly Gln Asn Leu Leu Gln Thr Gln Asp His Ala
                980                 985                 990

Lys Ala Pro Lys Ser Glu Lys Gly  Lys Ile Thr Lys Met  Pro Cys Gln
                995                 1000                1005

Ser Leu  Gln Pro Glu Pro Ile  Asn Thr Pro Thr His  Thr Lys Gln
    1010                 1015                 1020

Gln Leu  Lys Ala Ser Leu Gly  Lys Val Gly Val Lys  Glu Glu Leu
    1025                 1030                 1035
```

```
Leu Ala Val Gly Lys Phe Thr Arg Thr Ser Gly Glu Thr Thr His
1040                 1045                1050

Thr His Arg Glu Pro Ala Gly Asp Gly Lys Ser Ile Arg Thr Phe
1055                 1060                1065

Lys Glu Ser Pro Lys Gln Ile Leu Asp Pro Ala Ala Arg Val Thr
1070                 1075                1080

Gly Met Lys Lys Trp Pro Arg Thr Pro Lys Glu Glu Ala Gln Ser
1085                 1090                1095

Leu Glu Asp Leu Ala Gly Phe Lys Glu Leu Phe Gln Thr Pro Gly
1100                 1105                1110

Pro Ser Glu Glu Ser Met Thr Asp Glu Lys Thr Thr Lys Ile Ala
1115                 1120                1125

Cys Lys Ser Pro Pro Pro Glu Ser Val Asp Thr Pro Thr Ser Thr
1130                 1135                1140

Lys Gln Trp Pro Lys Arg Ser Leu Arg Lys Ala Asp Val Glu Glu
1145                 1150                1155

Glu Phe Leu Ala Leu Arg Lys Leu Thr Pro Ser Ala Gly Lys Ala
1160                 1165                1170

Met Leu Thr Pro Lys Pro Ala Gly Gly Asp Glu Lys Asp Ile Lys
1175                 1180                1185

Ala Phe Met Gly Thr Pro Val Gln Lys Leu Asp Leu Ala Gly Thr
1190                 1195                1200

Leu Pro Gly Ser Lys Arg Gln Leu Gln Thr Pro Lys Glu Lys Ala
1205                 1210                1215

Gln Ala Leu Glu Asp Leu Ala Gly Phe Lys Glu Leu Phe Gln Thr
1220                 1225                1230

Pro Gly His Thr Glu Glu Leu Val Ala Ala Gly Lys Thr Thr Lys
1235                 1240                1245

Ile Pro Cys Asp Ser Pro Gln Ser Asp Pro Val Asp Thr Pro Thr
1250                 1255                1260

Ser Thr Lys Gln Arg Pro Lys Arg Ser Ile Arg Lys Ala Asp Val
1265                 1270                1275

Glu Gly Glu Leu Leu Ala Cys Arg Asn Leu Met Pro Ser Ala Gly
1280                 1285                1290

Lys Ala Met His Thr Pro Lys Pro Ser Val Gly Glu Glu Lys Asp
1295                 1300                1305

Ile Ile Ile Phe Val Gly Thr Pro Val Gln Lys Leu Asp Leu Thr
1310                 1315                1320

Glu Asn Leu Thr Gly Ser Lys Arg Arg Pro Gln Thr Pro Lys Glu
1325                 1330                1335

Glu Ala Gln Ala Leu Glu Asp Leu Thr Gly Phe Lys Glu Leu Phe
1340                 1345                1350

Gln Thr Pro Gly His Thr Glu Glu Ala Val Ala Ala Gly Lys Thr
1355                 1360                1365

Thr Lys Met Pro Cys Glu Ser Ser Pro Pro Glu Ser Ala Asp Thr
1370                 1375                1380

Pro Thr Ser Thr Arg Arg Gln Pro Lys Thr Pro Leu Glu Lys Arg
1385                 1390                1395

Asp Val Gln Lys Glu Leu Ser Ala Leu Lys Lys Leu Thr Gln Thr
1400                 1405                1410

Ser Gly Glu Thr Thr His Thr Asp Lys Val Pro Gly Gly Glu Asp
1415                 1420                1425

Lys Ser Ile Asn Ala Phe Arg Glu Thr Ala Lys Gln Lys Leu Asp
```

```
            1430              1435              1440

Pro Ala Ala Ser Val Thr Gly Ser Lys Arg His Pro Lys Thr Lys
    1445              1450              1455

Glu Lys Ala Gln Pro Leu Glu Asp Leu Ala Gly Leu Lys Glu Leu
    1460              1465              1470

Phe Gln Thr Pro Val Cys Thr Asp Lys Pro Thr Thr His Glu Lys
    1475              1480              1485

Thr Thr Lys Ile Ala Cys Arg Ser Gln Pro Asp Pro Val Asp Thr
    1490              1495              1500

Pro Thr Ser Ser Lys Pro Gln Ser Lys Arg Ser Leu Arg Lys Val
    1505              1510              1515

Asp Val Glu Glu Glu Phe Phe Ala Leu Arg Lys Arg Thr Pro Ser
    1520              1525              1530

Ala Gly Lys Ala Met His Thr Pro Lys Pro Ala Val Ser Gly Glu
    1535              1540              1545

Lys Asn Ile Tyr Ala Phe Met Gly Thr Pro Val Gln Lys Leu Asp
    1550              1555              1560

Leu Thr Glu Asn Leu Thr Gly Ser Lys Arg Arg Leu Gln Thr Pro
    1565              1570              1575

Lys Glu Lys Ala Gln Ala Leu Glu Asp Leu Ala Gly Phe Lys Glu
    1580              1585              1590

Leu Phe Gln Thr Arg Gly His Thr Glu Glu Ser Met Thr Asn Asp
    1595              1600              1605

Lys Thr Ala Lys Val Ala Cys Lys Ser Ser Gln Pro Asp Pro Asp
    1610              1615              1620

Lys Asn Pro Ala Ser Ser Lys Arg Arg Leu Lys Thr Ser Leu Gly
    1625              1630              1635

Lys Val Gly Val Lys Glu Glu Leu Leu Ala Val Gly Lys Leu Thr
    1640              1645              1650

Gln Thr Ser Gly Glu Thr Thr His Thr His Thr Glu Pro Thr Gly
    1655              1660              1665

Asp Gly Lys Ser Met Lys Ala Phe Met Glu Ser Pro Lys Gln Ile
    1670              1675              1680

Leu Asp Ser Ala Ala Ser Leu Thr Gly Ser Lys Arg Gln Leu Arg
    1685              1690              1695

Thr Pro Lys Gly Lys Ser Glu Val Pro Glu Asp Leu Ala Gly Phe
    1700              1705              1710

Ile Glu Leu Phe Gln Thr Pro Ser His Thr Lys Glu Ser Met Thr
    1715              1720              1725

Asn Glu Lys Thr Thr Lys Val Ser Tyr Arg Ala Ser Gln Pro Asp
    1730              1735              1740

Leu Val Asp Thr Pro Thr Ser Ser Lys Pro Gln Pro Lys Arg Ser
    1745              1750              1755

Leu Arg Lys Ala Asp Thr Glu Glu Glu Phe Leu Ala Phe Arg Lys
    1760              1765              1770

Gln Thr Pro Ser Ala Gly Lys Ala Met His Thr Pro Lys Pro Ala
    1775              1780              1785

Val Gly Glu Glu Lys Asp Ile Asn Thr Phe Leu Gly Thr Pro Val
    1790              1795              1800

Gln Lys Leu Asp Gln Pro Gly Asn Leu Pro Gly Ser Asn Arg Arg
    1805              1810              1815

Leu Gln Thr Arg Lys Glu Lys Ala Gln Ala Leu Glu Glu Leu Thr
    1820              1825              1830
```

```
Gly Phe Arg Glu Leu Phe Gln Thr Pro Cys Thr Asp Asn Pro Thr
1835                1840                1845

Thr Asp Glu Lys Thr Thr Lys Lys Ile Leu Cys Lys Ser Pro Gln
1850                1855                1860

Ser Asp Pro Ala Asp Thr Pro Thr Asn Thr Lys Gln Arg Pro Lys
1865                1870                1875

Arg Ser Leu Lys Lys Ala Asp Val Glu Glu Phe Leu Ala Phe
1880                1885                1890

Arg Lys Leu Thr Pro Ser Ala Gly Lys Ala Met His Thr Pro Lys
1895                1900                1905

Ala Ala Val Gly Glu Glu Lys Asp Ile Asn Thr Phe Val Gly Thr
1910                1915                1920

Pro Val Glu Lys Leu Asp Leu Leu Gly Asn Leu Pro Gly Ser Lys
1925                1930                1935

Arg Arg Pro Gln Thr Pro Lys Glu Lys Ala Lys Ala Leu Glu Asp
1940                1945                1950

Leu Ala Gly Phe Lys Glu Leu Phe Gln Thr Pro Gly His Thr Glu
1955                1960                1965

Glu Ser Met Thr Asp Asp Lys Ile Thr Glu Val Ser Cys Lys Ser
1970                1975                1980

Pro Gln Pro Asp Pro Val Lys Thr Pro Thr Ser Ser Lys Gln Arg
1985                1990                1995

Leu Lys Ile Ser Leu Gly Lys Val Gly Val Lys Glu Glu Val Leu
2000                2005                2010

Pro Val Gly Lys Leu Thr Gln Thr Ser Gly Lys Thr Thr Gln Thr
2015                2020                2025

His Arg Glu Thr Ala Gly Asp Gly Lys Ser Ile Lys Ala Phe Lys
2030                2035                2040

Glu Ser Ala Lys Gln Met Leu Asp Pro Ala Asn Tyr Gly Thr Gly
2045                2050                2055

Met Glu Arg Trp Pro Arg Thr Pro Lys Glu Glu Ala Gln Ser Leu
2060                2065                2070

Glu Asp Leu Ala Gly Phe Lys Glu Leu Phe Gln Thr Pro Asp His
2075                2080                2085

Thr Glu Glu Ser Thr Thr Asp Asp Lys Thr Thr Lys Ile Ala Cys
2090                2095                2100

Lys Ser Pro Pro Pro Glu Ser Met Asp Thr Pro Thr Ser Thr Arg
2105                2110                2115

Arg Arg Pro Lys Thr Pro Leu Gly Lys Arg Asp Ile Val Glu Glu
2120                2125                2130

Leu Ser Ala Leu Lys Gln Leu Thr Gln Thr Thr His Thr Asp Lys
2135                2140                2145

Val Pro Gly Asp Glu Asp Lys Gly Ile Asn Val Phe Arg Glu Thr
2150                2155                2160

Ala Lys Gln Lys Leu Asp Pro Ala Ala Ser Val Thr Gly Ser Lys
2165                2170                2175

Arg Gln Pro Arg Thr Pro Lys Gly Lys Ala Gln Pro Leu Glu Asp
2180                2185                2190

Leu Ala Gly Leu Lys Glu Leu Phe Gln Thr Pro Ile Cys Thr Asp
2195                2200                2205

Lys Pro Thr Thr His Glu Lys Thr Thr Lys Ile Ala Cys Arg Ser
2210                2215                2220
```

```
Pro Gln Pro Asp Pro Val Gly Thr Pro Thr Ile Phe Lys Pro Gln
2225                2230                2235

Ser Lys Arg Ser Leu Arg Lys Ala Asp Val Glu Glu Ser Leu
2240                2245                2250

Ala Leu Arg Lys Arg Thr Pro Ser Val Gly Lys Ala Met Asp Thr
2255                2260                2265

Pro Lys Pro Ala Gly Gly Asp Glu Lys Asp Met Lys Ala Phe Met
2270                2275                2280

Gly Thr Pro Val Gln Lys Leu Asp Leu Pro Gly Asn Leu Pro Gly
2285                2290                2295

Ser Lys Arg Trp Pro Gln Thr Pro Lys Glu Lys Ala Gln Ala Leu
2300                2305                2310

Glu Asp Leu Ala Gly Phe Lys Glu Leu Phe Gln Thr Pro Gly Thr
2315                2320                2325

Asp Lys Pro Thr Thr Asp Glu Lys Thr Thr Lys Ile Ala Cys Lys
2330                2335                2340

Ser Pro Gln Pro Asp Pro Val Asp Thr Pro Ala Ser Thr Lys Gln
2345                2350                2355

Arg Pro Lys Arg Asn Leu Arg Lys Ala Asp Val Glu Glu Glu Phe
2360                2365                2370

Leu Ala Leu Arg Lys Arg Thr Pro Ser Ala Gly Lys Ala Met Asp
2375                2380                2385

Thr Pro Lys Pro Ala Val Ser Asp Glu Lys Asn Ile Asn Thr Phe
2390                2395                2400

Val Glu Thr Pro Val Gln Lys Leu Asp Leu Leu Gly Asn Leu Pro
2405                2410                2415

Gly Ser Lys Arg Gln Pro Gln Thr Pro Lys Glu Lys Ala Glu Ala
2420                2425                2430

Leu Glu Asp Leu Val Gly Phe Lys Glu Leu Phe Gln Thr Pro Gly
2435                2440                2445

His Thr Glu Glu Ser Met Thr Asp Asp Lys Ile Thr Glu Val Ser
2450                2455                2460

Cys Lys Ser Pro Gln Pro Glu Ser Phe Lys Thr Ser Arg Ser Ser
2465                2470                2475

Lys Gln Arg Leu Lys Ile Pro Leu Val Lys Val Asp Met Lys Glu
2480                2485                2490

Glu Pro Leu Ala Val Ser Lys Leu Thr Arg Thr Ser Gly Glu Thr
2495                2500                2505

Thr Gln Thr His Thr Glu Pro Thr Gly Asp Ser Lys Ser Ile Lys
2510                2515                2520

Ala Phe Lys Glu Ser Pro Lys Gln Ile Leu Asp Pro Ala Ala Ser
2525                2530                2535

Val Thr Gly Ser Arg Arg Gln Leu Arg Thr Arg Lys Glu Lys Ala
2540                2545                2550

Arg Ala Leu Glu Asp Leu Val Asp Phe Lys Glu Leu Phe Ser Ala
2555                2560                2565

Pro Gly His Thr Glu Glu Ser Met Thr Ile Asp Lys Asn Thr Lys
2570                2575                2580

Ile Pro Cys Lys Ser Pro Pro Pro Glu Leu Thr Asp Thr Ala Thr
2585                2590                2595

Ser Thr Lys Arg Cys Pro Lys Thr Arg Pro Arg Lys Glu Val Lys
2600                2605                2610

Glu Glu Leu Ser Ala Val Glu Arg Leu Thr Gln Thr Ser Gly Gln
```

```
                2615                2620                2625

Ser Thr His Thr His Lys Glu Pro Ala Ser Gly Asp Glu Gly Ile
        2630                2635                2640

Lys Val Leu Lys Gln Arg Ala Lys Lys Pro Asn Pro Val Glu
        2645                2650                2655

Glu Glu Pro Ser Arg Arg Pro Arg Ala Pro Lys Glu Lys Ala
        2660                2665                2670

Gln Pro Leu Glu Asp Leu Ala Gly Phe Thr Glu Leu Ser Glu Thr
        2675                2680                2685

Ser Gly His Thr Gln Glu Ser Leu Thr Ala Gly Lys Ala Thr Lys
        2690                2695                2700

Ile Pro Cys Glu Ser Pro Pro Leu Glu Val Val Asp Thr Thr Ala
        2705                2710                2715

Ser Thr Lys Arg His Leu Arg Thr Arg Val Gln Lys Val Gln Val
        2720                2725                2730

Lys Glu Glu Pro Ser Ala Val Lys Phe Thr Gln Thr Ser Gly Glu
        2735                2740                2745

Thr Thr Asp Ala Asp Lys Glu Pro Ala Gly Glu Asp Lys Gly Ile
        2750                2755                2760

Lys Ala Leu Lys Glu Ser Ala Lys Gln Thr Pro Ala Pro Ala Ala
        2765                2770                2775

Ser Val Thr Gly Ser Arg Arg Arg Pro Arg Ala Pro Arg Glu Ser
        2780                2785                2790

Ala Gln Ala Ile Glu Asp Leu Ala Gly Phe Lys Asp Pro Ala Ala
        2795                2800                2805

Gly His Thr Glu Glu Ser Met Thr Asp Asp Lys Thr Thr Lys Ile
        2810                2815                2820

Pro Cys Lys Ser Ser Pro Glu Leu Glu Asp Thr Ala Thr Ser Ser
        2825                2830                2835

Lys Arg Arg Pro Arg Thr Arg Ala Gln Lys Val Glu Val Lys Glu
        2840                2845                2850

Glu Leu Leu Ala Val Gly Lys Leu Thr Gln Thr Ser Gly Glu Thr
        2855                2860                2865

Thr His Thr Asp Lys Glu Pro Val Gly Glu Gly Lys Gly Thr Lys
        2870                2875                2880

Ala Phe Lys Gln Pro Ala Lys Arg Lys Leu Asp Ala Glu Asp Val
        2885                2890                2895

Ile Gly Ser Arg Arg Gln Pro Arg Ala Pro Lys Glu Lys Ala Gln
        2900                2905                2910

Pro Leu Glu Asp Leu Ala Ser Phe Gln Glu Leu Ser Gln Thr Pro
        2915                2920                2925

Gly His Thr Glu Glu Leu Ala Asn Gly Ala Ala Asp Ser Phe Thr
        2930                2935                2940

Ser Ala Pro Lys Gln Thr Pro Asp Ser Gly Lys Pro Leu Lys Ile
        2945                2950                2955

Ser Arg Arg Val Leu Arg Ala Pro Lys Val Glu Pro Val Gly Asp
        2960                2965                2970

Val Val Ser Thr Arg Asp Pro Val Lys Ser Gln Ser Lys Ser Asn
        2975                2980                2985

Thr Ser Leu Pro Pro Leu Pro Phe Lys Arg Gly Gly Lys Asp
        2990                2995                3000

Gly Ser Val Thr Gly Thr Lys Arg Leu Arg Cys Met Pro Ala Pro
        3005                3010                3015
```

Glu Glu Ile Val Glu Glu Leu Pro Ala Ser Lys Lys Gln Arg Val
3020              3025              3030

Ala Pro Arg Ala Arg Gly Lys Ser Ser Glu Pro Val Val Ile Met
3035              3040              3045

Lys Arg Ser Leu Arg Thr Ser Ala Lys Arg Ile Glu Pro Ala Glu
3050              3055              3060

Glu Leu Asn Ser Asn Asp Met Lys Thr Asn Lys Glu Glu His Lys
3065              3070              3075

Leu Gln Asp Ser Val Pro Glu Asn Lys Gly Ile Ser Leu Arg Ser
3080              3085              3090

Arg Arg Gln Asn Lys Thr Glu Ala Glu Gln Gln Ile Thr Glu Val
3095              3100              3105

Phe Val Leu Ala Glu Arg Ile Glu Ile Asn Arg Asn Glu Lys Lys
3110              3115              3120

Pro Met Lys Thr Ser Pro Glu Met Asp Ile Gln Asn Pro Asp Asp
3125              3130              3135

Gly Ala Arg Lys Pro Ile Pro Arg Asp Lys Val Thr Glu Asn Lys
3140              3145              3150

Arg Cys Leu Arg Ser Ala Arg Gln Asn Glu Ser Ser Gln Pro Lys
3155              3160              3165

Val Ala Glu Glu Ser Gly Gly Gln Lys Ser Ala Lys Val Leu Met
3170              3175              3180

Gln Asn Gln Lys Gly Lys Gly Glu Ala Gly Asn Ser Asp Ser Met
3185              3190              3195

Cys Leu Arg Ser Arg Lys Thr Lys Ser Gln Pro Ala Ala Ser Thr
3200              3205              3210

Leu Glu Ser Lys Ser Val Gln Arg Val Thr Arg Ser Val Lys Arg
3215              3220              3225

Cys Ala Glu Asn Pro Lys Lys Ala Glu Asp Asn Val Cys Val Lys
3230              3235              3240

Lys Ile Arg Thr Arg Ser His Arg Asp Ser Glu Asp Ile
3245              3250              3255

<210> SEQ ID NO 14
<211> LENGTH: 169
<212> TYPE: PRT
<213> ORGANISM: Homo sapiens

<400> SEQUENCE: 14

Met Ala Pro Pro Trp Val Pro Ala Met Gly Phe Thr Leu Ala Pro Ser
1               5                   10                  15

Leu Gly Cys Phe Val Gly Ser Arg Phe Val His Gly Glu Gly Leu Arg
                20                  25                  30

Trp Tyr Ala Gly Leu Gln Lys Pro Ser Trp His Pro Pro His Trp Val
            35                  40                  45

Leu Gly Pro Val Trp Gly Thr Leu Tyr Ser Ala Met Gly Tyr Gly Ser
        50                  55                  60

Tyr Leu Val Trp Lys Glu Leu Gly Gly Phe Thr Glu Lys Ala Val Val
65                  70                  75                  80

Pro Leu Gly Leu Tyr Thr Gly Gln Leu Ala Leu Asn Trp Ala Trp Pro
                85                  90                  95

Pro Ile Phe Phe Gly Ala Arg Gln Met Gly Trp Ala Leu Val Asp Leu
            100                 105                 110

Leu Leu Val Ser Gly Ala Ala Ala Ala Thr Thr Val Ala Trp Tyr Gln
        115                 120                 125

-continued

```
Val Ser Pro Leu Ala Ala Arg Leu Leu Tyr Pro Tyr Leu Ala Trp Leu
    130                 135                 140

Ala Phe Thr Thr Thr Leu Asn Tyr Cys Val Trp Arg Asp Asn His Gly
145                 150                 155                 160

Trp Arg Gly Gly Arg Arg Leu Pro Glu
                165

<210> SEQ ID NO 15
<211> LENGTH: 102
<212> TYPE: PRT
<213> ORGANISM: Homo sapiens

<400> SEQUENCE: 15

Met Ala Pro His Leu Leu Trp Cys Pro Thr Asn Gly Leu Gly Leu Gly
1               5                   10                  15

Gly Ser Pro Ala Gly Gln Trp Gly Gly Ser His Tyr Arg Gly Leu
            20                  25                  30

Val Pro Gly Glu Pro Ala Gly Arg Pro Pro Ala Leu Pro Leu Pro Gly
            35                  40                  45

Leu Ala Gly Leu His Asp His Thr Gln Leu Leu Arg Met Ala Gly Gln
    50                  55                  60

Pro Trp Leu Ala Trp Gly Thr Ala Ala Ala Arg Val Ser Ala Arg Pro
65                  70                  75                  80

Thr Arg Asp Cys Ser Cys Thr Ser Arg Cys His His Ala Cys Asp Val
                85                  90                  95

Val Ala Val Thr Leu Ser
            100
```

METHODS FOR DIAGNOSING ORAL OR ORAL-PHARYNGEAL CANCER

RELATED APPLICATION/S

This application claims the benefit of priority under 35 USC 119(e) of U.S. Provisional Patent Application No. 61/213,525 filed Jun. 16, 2009, the contents of which are incorporated herein by reference in their entirety.

STATEMENT

The ASCII file, entitled 48593SequenceListing.txt, created on Jun. 16, 2010, comprising 71,837 bytes, submitted concurrently with the filing of this application is incorporated herein by reference.

FIELD AND BACKGROUND OF THE INVENTION

The present invention, in some embodiments thereof, relates to methods and kits for diagnosing cancer and, more particularly, but not exclusively, to the diagnosis of oral and oral pharyngeal cancer.

Oral cancer such as oral squamous cell carcinoma (OSCC) is a common human malignancy, with an increasing incidence (especially in younger people) and a 5-year mortality rate of approximately 50%, which has not changed significantly in more than 50 years. Treatment results in a relatively high rate of related morbidity, due to frequent significant mutilation and compromised functions. OSCC includes both mobile (oral) and base of tongue cancer lesions. Most often an oral cancer lesion is located at the lateral border of the tongue, while one located at the base of tongue is considered especially lethal. Clinically, it is important to note that the therapeutic modality currently offered to patients is based on traditional stage-predicting indices [based mostly on the classification of malignant tumors (TNM) Criteria] and on histological grading. Unfortunately, these predictors are subjective and relatively unreliable, as often two tumors with identical staging and grading behave in a different manner, and while one responds to therapy, the other is lethal.

Salivary testing is a non-invasive alternative to serum testing, an effective modality for diagnosis oral cancer, as well as for monitoring the post therapy status of the patient. Follow-up of patients who have undergone treatment for OSCC is done routinely and often in order to detect recurrences soon after they occur. The development of salivary diagnostic tools for these patients is pivotal. Home testing kits would further facilitate salivary testing as a diagnostic aid, enabling patients, especially those who live far from treatment centers to self-monitor at home. Furthermore, salivary markers are of particular importance from a clinical point of view, since there is direct contact between the oral cancer lesion and saliva. Even more so, salivary analysis has been shown to be a useful diagnostic tool for other distant malignancies, such as breast cancer.

Circulatory tumor markers for OSCC were investigated in various studies and showed relatively moderate sensitivity and specificity values with relation to diagnosis, prognosis predicting, or treatment monitoring.

For example, Kurokawa et al. analyzed circulatory carcinoembryonic antigen (CEA), SCC, immunosuppressive acidic protein, and Cyfra concentrations in OSCC patients and found sensitivity and accuracy values of 81% and 77.8%, respectively. When CEA, SCC, and immunosuppressive acidic protein were analyzed alone, the values were 69% and 90.3%, respectively [Kurokawa H, et al. Int J Oral Maxillofac Surg 1993; 22:35-8; Kurokawa H, et al J Oral Maxillofac Surg 1997; 55:964-6].

WO2008/001357 teaches methods and kits for diagnosing cancer by determining a level and/or activity of at least one saliva secreted marker in a saliva sample of the subject wherein an alteration in the marker with respect to an unaffected saliva sample is indicative of the cancer.

ADDITIONAL RELATED ART

Sathyan et al. Oral Oncol. 2006 42(6):607-13;
Wang et al. 2006 Oral Oncol. 42(6):625-31;
Liu et al. 2003 Head Neck 25(4):280-8;
Kawakubo et al. Oncol. Rep. 2005 14(6):1453-9;
Paz-Elizur et al. Cancer Res. 2006 66(24):11683-9;
van Oijen et al. J. Oral Pathol. Med. 1998 27(4):147-52;
Chen et al. Neoplasia 2008 10(12):1393-401;
Xia et al. (2000) Oncogene 19:2398-403;
Yasumatsu et al. Head Neck 2001 23(11):962-6;
Vairaktaris et al. 2008 Eur. J. Surg. Oncol. 34:450-5

SUMMARY OF THE INVENTION

According to an aspect of some embodiments of the present invention there is provided a method of diagnosing cancer in a subject in need thereof, the method comprising determining a level or activity of at least one marker in a saliva sample of the subject, wherein a significant alteration in the level or the activity of the marker with respect to an unaffected saliva sample is indicative of the cancer, wherein the saliva marker is selected from the group consisting of Cyclin D1, phospho-Src, 8-oxoguanine DNA glycosylase (OGG1), Maspin, KI67 and translocator protein 18 kDa (TSPO), wherein the cancer is oral cancer, or oral pharyngeal cancer.

According to an aspect of some embodiments of the present invention there is provided a method of diagnosing or determining prognosis of oral cancer or oral pharyngeal cancer in a subject in need thereof, the method comprising determining a level of translocator protein 18 kDa (TSPO) in an oral tissue biopsy of the subject, wherein a significant upregulation in the level or the activity of the translocator protein 18 kDa (TSPO) with respect to an unaffected oral tissue sample is indicative of the oral cancer, or oral pharyngeal cancer and is inversely correlated with prognosis.

According to some embodiments of the invention, the method further comprising informing the subject of presence or absence of oral cancer following the determining.

According to some embodiments of the invention, the method further comprising corroborating the diagnosis using a diagnostic assay selected from the group comprising tissue biopsy, oral examination, dental X-ray, head X-ray, CT scan, ultrasonography and MRI.

According to some embodiments of the invention, the oral cancer comprises oral squamous cell carcinoma.

According to some embodiments of the invention, the at least one marker comprises at least two markers.

According to some embodiments of the invention, the at least two markers are selected from the group consisting of Maspin and Cyclin D1, Carbonyls and Cyclin D1, Carbonyls and Maspin, Carbonyls and KI67, Cyclin D1 and MMP9, and Maspin and OGG1.

According to some embodiments of the invention, the determining is effected at the protein level.

According to some embodiments of the invention, the saliva sample is a cellular fraction of saliva.

According to some embodiments of the invention, the determining is effected by Enzyme-linked immunosorbent assay (ELISA).

According to some embodiments of the invention, the at least one marker is TSPO the determining is effected by a PK 11195 binding assay.

According to an aspect of some embodiments of the present invention there is provided a device identified for diagnosing oral cancer or oral pharyngeal cancer in a subject, the device comprising a support and at least one agent for specifically determining a level and/or activity of at least one saliva marker in a saliva sample of the subject attached to the support, the saliva marker being selected from the group consisting of phospho-Src, Cyclin D1, 8-oxoguanine DNA glycosylase (OGG1), Maspin and KI67.

According to some embodiments of the invention, the at least one agent is an antibody.

According to some embodiments of the invention, the device is a lateral flow device.

According to some embodiments of the invention, the device is a dipstick or a cartridge.

According to an aspect of some embodiments of the present invention there is provided a kit for diagnosing oral cancer or oral pharyngeal cancer in a subject, the kit comprising a packaging material a printed identification for use in said diagnosis and at least one antibody for a salivary marker selected from the group consisting of Cyclin D1, phospho-Src, 8-oxoguanine DNA glycosylase (OGG1), Maspin and KI67.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 1A-B are photomicrographs showing cytoplasmaic, slightly granular staining of well to moderately differentiated carcinoma (FIG. 2A); and cytoplasmaic, slightly granular staining of moderately to poorly differentiated carcinoma (FIG. 2B).

Figure 2:
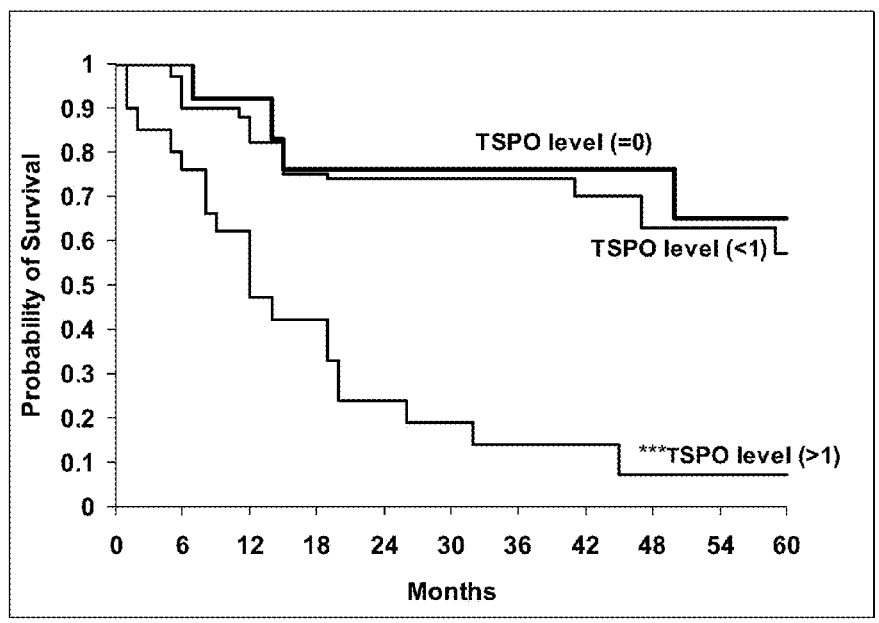

FIG. 2 is a graph showing cumulative probability of survival as a function of TSPO level (0 vs 1 vs>1), (n=69). The probability of survival of patients with TSPO level (=0) at 60 month was 65% while the probability of survival of patients with TSPO level (>1) at 60 month was 7% only.

Figure 3:
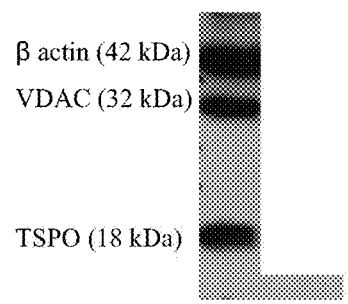

FIG. 3 is a photograph of a representative Western blot analysis of TSPO, VDAC and β actin proteins in the SCC-25 cell line growing under normal physiological conditions illustrating protein expression of TSPO, VDAC, and beta-actin in oral cancer cell lines.

FIGS. 4A-B are Scatchard plots of [$^3$H]PK 11195 (0.2-6 nM final concentration) illustrating binding to SCC-25 human oral cancer cell (n=16). Explanation of abbreviations: B=concentration of Bound ligand, B/F=concentration of Bound ligand over concentration of Free ligand.

Figure 5:
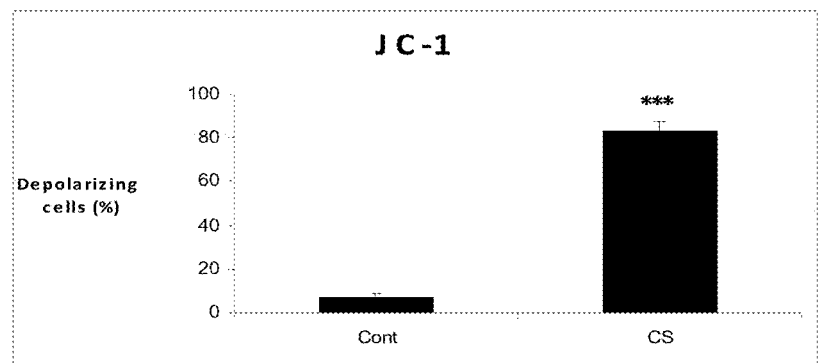

FIG. 5 is a bar graph illustrating collapse of the mitochondrial membrane potential after exposure of SCC-25 cells to cigarette smoke. Exposure of SCC-25 oral cancer cells in culture to cigarette smoke (CS) causes collapse of $\Delta\psi_m$ in the majority of the cells, as indicated by unpolymerized JC-1 levels. *** $P<0.001$ compared to control (n=6)

FIGS. 6A-B are bar graphs and photographs illustrating TSPO binding in saliva of cigarette smokers and non-smokers. (A). Mean±SE [$^3$H]PK 11195 specific binding values (final concentrations 6 nM) in saliva of non-smoking individuals (Control, n=16) and heavy smokers (Smokers, n=9) (p<0.05). (B). A representative Western blot analysis of TSPO, VDAC and β actin proteins in saliva of a non-smoking individual (termed Non-smoker), and a smoking individual (termed Smoker).

Figure 7:
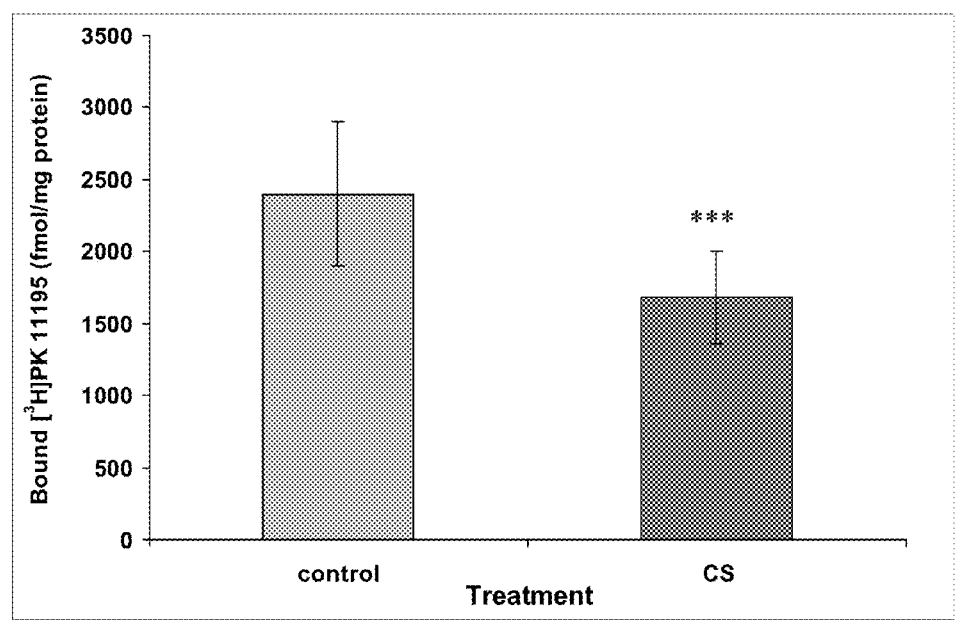

FIG. 7 is a bar graph illustrating TSPO binding in saliva exposed to cigarette smoke in vitro. Binding of [$^3$H]PK 11195 (final concentration 6 nM) in control saliva and saliva (collected from non smoking healthy individuals) exposed in vitro to cigarette smoke. The results are expressed as mean values±SE (n=34, p<0.001).

Figure 8:
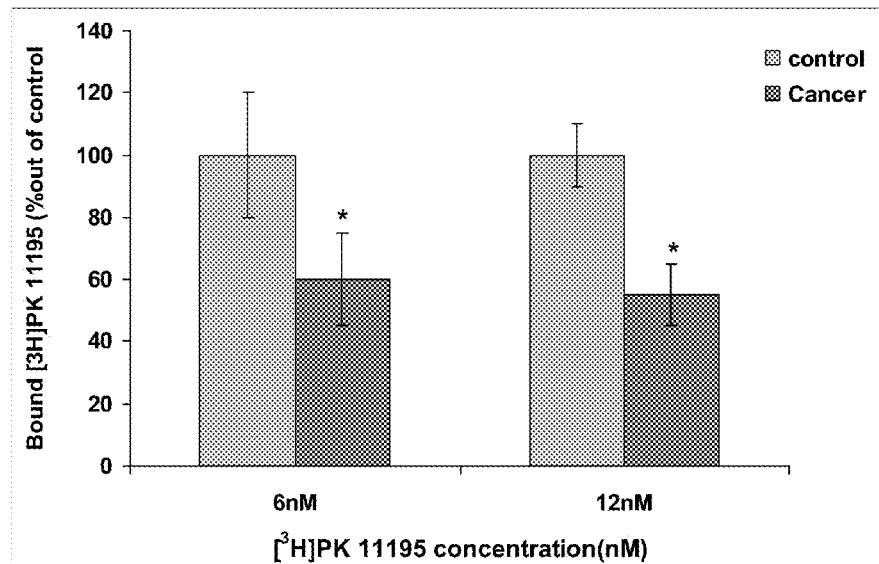

FIG. 8 is a bar graph illustrating TSPO binding in saliva of oral cancer patients and healthy persons. Mean±SE [$^3$H]PK 11195 specific binding values (final concentrations 6 nM and 12 nM) in saliva of healthy individuals (Control, n=6) and oral cancer patients (Cancer, n=13). p<0.05 for both concentrations compared to control.

Figure 9:
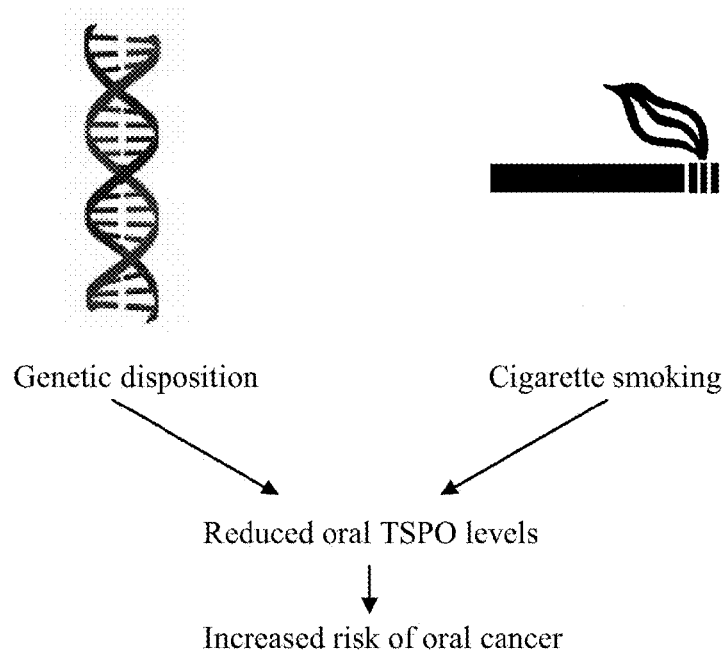

FIG. 9 is a schematic presentation suggested for the implication of TSPO in the pathogenesis of oral cancer. Both cigarette smoke and genetic disposition appear to lead to reduced TSPO binding in the saliva which appears to correlate with an increased susceptibility to tongue cancer.

Figure 10:
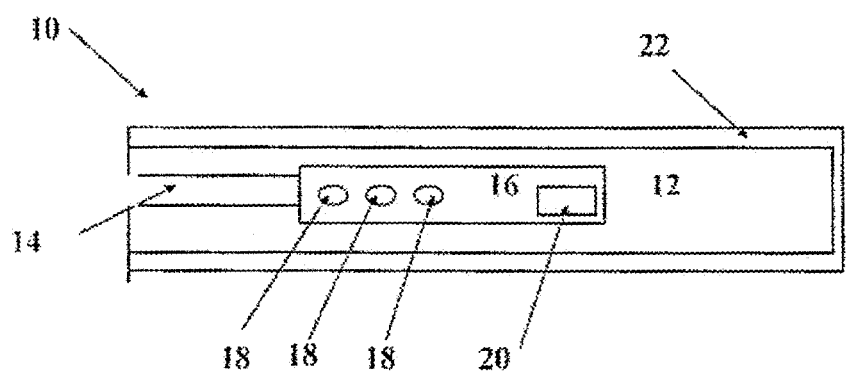

FIG. 10 shows an embodiment of a device according to some teachings of the present invention as seen in a longitudinal section.

DESCRIPTION OF EMBODIMENTS OF THE INVENTION

The present invention, in some embodiments thereof, relates to methods and kits for diagnosing cancer such as oral and oral pharyngeal cancer.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Whilst reducing the present invention to practice, the present inventors uncovered a group of salivary and tissue-associated biomarkers in oral cancer patients which serve as accurate predictors of the disease. Furthermore, the present inventors showed that concurrent analysis of a combination of these markers may significantly increase the diagnostic accuracy of the test to a clinically acceptable level. As is illustrated hereinbelow and in the Examples section which follows, the present inventors based their findings on two studies.

First (described in Example 1 of the Examples section which follows), 19 tongue cancer patients were tested for 8 salivary markers related to oxidative stress, DNA repair, carcinogenesis, metastasis and cellular proliferation and death. Five of the markers were increased in the cancer patients by 39%-246%: carbonyls, LDH, MMP-9, Ki67 and CycD1 ($p \leq 0.01$). The other 3 markers were decreased in the cancer patients by 16%-29%: OGG1, phospho-Src and Maspin ($p \leq 0.01$). The increase in salivary carbonyls was profound (by 246%, p=0.012) and especially significant were the alterations in CycD1 (an increase by 87%, p=0.000006) and in Maspin (a decrease by 29%, p=0.007). The sensitivity values of these 8 analyzed markers were in the range of 58%-100% while the specificity values were in the range of 42%-100%. The sensitivity and specificity values were especially high for the CycD1 and Maspin markers, 100% for each value of each marker. These were also quite high for the carbonyls, 90% and 80% respectively and for the MMP-9, 100% and 79% respectively.

Second (see Examples 2 and 3 of the Examples section which follows), TSPO expression was analyzed in 69 oral (tongue) cancer patients and TSPO binding was examined in tongue cancer cell lines, in the saliva of tongue cancer patients, in the saliva of heavy cigarette smokers and in saliva samples of non smoking healthy controls which was exposed to CS in vitro. Concurrently Western blot analysis, cell viability and protein level determination were performed. TSPO expression was significantly enhanced in oral cancer tumors and its levels correlated conversely with patient survival (in situ). The 5 year survival probability dropped from 65% in patients whose tumors were negatively stained to TSPO to 7% only in patients whose tumors highly expressed TSPO (p=0.0001), indicating that TSPO is central in the pathogenesis of oral cancer. This was substantially supported by the demonstrated significant reduction in salivary TSPO binding among oral cancer patients (by 40%, p=0.02). TSPO was found to be highly expressed in the human oral cancer cell lines SCC-25 and SCC-15, where its binding decreased by 56-72% (p=0.02) following CS exposure. A similar decrease in TSPO binding (by 53%, p=0.02) in heavy smokers and in saliva exposed to CS in vitro (by 30%, p=0.00006) was found. These results show that TSPO has a pathogenetic role in oral cancer, perhaps based on induced reduction in TSPO binding rendered by inborn genetic defects or by a later exposure to carcinogens such as those in CS, which may prevent TSPO from being able to perform its known anti cancer activity (by inducing apoptosis in transformed cells).

Thus, the above-mentioned tumor markers may be used as diagnostic tools for diagnosis, prognosis and post-operative monitoring purposes.

Thus, according to one aspect of the present invention, there is provided a method of diagnosing oral cancer or oral pharyngeal cancer in a subject in need thereof, the method comprising determining a level or activity of at least one marker in a saliva sample of the subject, wherein a significant alteration in the level or the activity of the marker with respect to an unaffected saliva sample is indicative of the cancer, wherein the saliva marker is selected from the group consisting of Cyclin D1, phospho-Src, Matrix Metallopeptidase-9 (MMP9), 8-oxoguanine DNA glycosylase (OGG1), Maspin, KI67 and translocator protein 18 kDa (TSPO).

According to an additional or an alternative embodiment, there is provided a method of diagnosing or determining prognosis of oral cancer or oral pharyngeal cancer in a subject in need thereof, the method comprising determining a level of translocator protein 18 kDa (TSPO) in an oral tissue biopsy of the subject, wherein a significant upregulation in the level or the activity of the translocator protein 18 kDa (TSPO) with respect to an unaffected oral tissue sample is indicative of the oral cancer, or oral pharyngeal cancer and is inversely correlated with prognosis (e.g., see Example 2 below).

As used herein "cyclin D1" refers to the mRNA or polypeptide products of the CCND1 gene (e.g., NC_000011.8 NT_078088.3, NP_444284.1 (SEQ ID NO: 1)).

As used herein "phosphor-Src" refers to the polypeptide product of the Src gene which is tyrosine phosphorylated at position 419 (Tyr 419). This corresponds to SEQ ID NO: 2.

As used herein "MMP-9" refers to the mRNA or polypeptide products of the matrix metallopeptidase 9 (gelatinase B, 92 kDa gelatinase, 92 kDa type IV collagenase (MMP9) gene [e.g., NC_000020.9 NT_011362.9, NP_004985.2 (SEQ ID NO: 3)].

As used herein "OGG-1" refers to the mRNA or polypeptide products of the 8-oxoguanine DNA glycosylase (OGG1) gene (e.g., NC_000003.10 NT_022517.17; NP_002533.1 NP_058212.1 NP_058213.1 NP_058214.1 NP_058434.1 NP_058436.1 NP_058437.1 NP_058438.1 (SEQ ID NOs: 4-11 respectively, describe the polypeptide sequences)).

As used herein "Maspin" (or "SerpinB5") refers to the mRNA or polypeptide products of the SERPINB5gene [e.g., NC_000018.8 NT_025028.13, NP_002630.2 (SEQ ID NO: 12)].

As used herein "KI67" refers to the mRNA or polypeptide products of the MKI67 gene [e.g., NC_000010.9 NT_008818.15, NP_002408.3 (SEQ ID NO: 13)].

As used herein "TSPO" refers to the mRNA or polypeptide products of the translocator protein (18 kDa) (TSPO) gene (e.g., NC_000022.9 NT_011520.11; NP_000705.2 NP_009295.2 [SEQ ID NO: 14 and 15 describe the polypeptide sequences)].

As used herein, the term "diagnosing" refers to determining the presence of a cancer, classifying a cancer, determining a severity of cancer (grade or stage), monitoring cancer progression, forecasting an outcome of the cancer and/or prospects of recovery.

The subject may be a healthy animal or human subject undergoing a routine well-being check up. Alternatively, the subject may be at risk of having cancer (e.g., a genetically predisposed subject, a subject with medical and/or family history of cancer, a subject who has been exposed to carcinogens, occupational hazard, environmental hazard] and/or a subject who exhibits suspicious clinical signs of cancer [e.g., blood in the stool or melena, unexplained pain, sweating, unexplained fever, unexplained loss of weight up to anorexia, changes in bowel habits (constipation and/or diarrhea), tenesmus (sense of incomplete defecation, for rectal cancer specifically), anemia and/or general weakness). According to another embodiment, the subject may be a diagnosed cancer patient and is performing a routine check-up, in-between treatments (such as for determining treatment course).

The term "cancer" as used herein, refers to a disease or disorder resulting from the proliferation of oncogenically transformed cells. Examples of particular cancers that may be diagnosed according to the method of the present invention include oral cancer, such as oral squamous cell carcinoma and oral pharyngeal cancer.

As used herein, the term "saliva" refers to the oral fluid typically made up of a combination of secretions from a number of sources (e.g., parotid, submandibular, sublingual, accessory glands, gingival mucosa and buccal mucosa) and comprises exfoliated cells or cell fragments.

The saliva analyzed according to the method of the present invention may be stimulated (e.g. by chewing on a piece of paraffin film or tart candy) or unstimulated. According to a preferred embodiment of this aspect of the present invention, the saliva is unstimulated (see Example 1).

Saliva specimens for testing can be collected following various methods known in the art. Proper conditions for generating unstimulated saliva have been described. (Nazaresh and Christiansen, J. Dent. Res. 61: 1158-1162 (1982)). Methods and devices for collecting saliva have also been described. (See also, U.S. Pat. No. 5,910,122 to D'Angelo; U.S. Pat. No. 5,714,341 to Thieme et al.; U.S. Pat. Nos. 5,335,673 and 5,103,836 to Goldstein et al.; U.S. Pat. No. 5,268,148 to Seymour; and U.S. Pat. No. 4,768,238 to Kleinberg et al., incorporated herein in their entirety by reference).

The saliva may be analyzed immediately following collection of the sample. Alternatively, salivary analysis according to the method of the present invention can be performed on a stored saliva sample. The saliva sample for testing can be preserved using methods and apparatuses known in the art. (See e.g., U.S. Pat. No. 5,968,746 to Schneider, hereby incorporated in its entirety by reference). The present invention also contemplates treatment of the saliva prior to analysis (for example, to reduce viscosity and to remove cellular material). Techniques used to remove debris include centrifugation and filtration. The viscosity of saliva can also be reduced by mixing a saliva sample with a cationic quaternary ammonium reagent. (See, U.S. Pat. No. 5,112,758 to Fellman et al., incorporated herein in its entirety by reference). It will be appreciated that for detection of secreted salivary markers, the sample may be centrifuged and the supernatant is used. Alternatively for the detection of cell associated markers (e.g., TSPO) the saliva is centrifuged and the cell pellet is subjected to lysis.

Oral tissue biopsy can be obtained using methods which are well known in the art (e.g., see Example 2). For example, tongue biopsy can be done using a needle. After numbing the area, the health care provider gently sticks the needle into the tongue and removes a tiny piece of tissue.

Some types of tongue biopsies remove a thin slice of tissue. Others are done under general anesthesia so that larger areas, such as lesion, growth, or other abnormal area of the tongue, may be removed and examined.

Other markers that may be analyzed according to the method of the present invention include, but are not limited to the antioxidant markers, (e.g. glutathione S-transferase (GST), Superoxide dismutase (SOD), ferrylmyoglobin and peroxidase); Metalloproteinase (e.g. Metalloproteinase 2 or Metalloproteinase 9); Benzodiazepine receptor or subunits thereof; Heparanase; amylase; lactate dehydrogenase (LDH); insulin-like growth factor (IGF); protein carbonyls, epidermal growth factor (EGF) and albumin. It will be appreciated that a combination of the markers of the present invention may be analyzed in order to diagnose the subject. Accordingly, the present invention anticipates analysis of two markers, three markers, four markers, five markers and six or more markers. Specific marker combinations with improved diagnostic value are provided in Table 2, below. Thus according to specific embodiments, the at least two markers are selected from the group consisting of Maspin and Cyclin D1, Carbonyls and Cyclin D1, Carbonyls and Maspin, Carbonyls and KI67, Cyclin D1 and MMP9, and Maspin and OGG1.

Expression and/or activity level of particular proteins present (i.e., cell associated or secreted) in the saliva can be determined using methods known in the arts.

Enzyme Linked Immunosorbent Assay (ELISA):

This method involves fixation of saliva containing a protein substrate to a surface such as a well of a microtiter plate. A substrate specific antibody coupled to an enzyme is applied and allowed to bind to the substrate. Presence of the antibody is then detected and quantitated by a colorimetric reaction employing the enzyme coupled to the antibody. Enzymes commonly employed in this method include horseradish peroxidase and alkaline phosphatase. If well calibrated and within the linear range of response, the amount of substrate present in the sample is proportional to the amount of color produced. A substrate standard is generally employed to improve quantitative accuracy.

Western Blot:

This method involves separation of a substrate from other protein by means of an acrylamide gel followed by transfer of the substrate to a membrane (e.g., nylon or PVDF). Presence of the substrate is then detected by antibodies specific to the substrate, which are in turn detected by antibody binding reagents. Antibody binding reagents may be, for example, protein A, or other antibodies. Antibody binding reagents may be radiolabeled or enzyme linked as described hereinabove. Detection may be by autoradiography, colorimetric reaction or chemiluminescence. This method allows both quantitation of an amount of substrate and determination of its identity by a relative position on the membrane which is indicative of a migration distance in the acrylamide gel during electrophoresis.

Radio-Immunoassay (RIA):

In one version, this method involves precipitation of the desired protein (i.e., the substrate) with a specific antibody and radiolabeled antibody binding protein (e.g., protein A labeled with $I^{125}$) immobilized on a precipitable carrier such as agarose beads. The number of counts in the precipitated pellet is proportional to the amount of substrate.

In an alternate version of the RIA, a labeled substrate and an unlabelled antibody binding protein are employed. A sample containing an unknown amount of substrate is added in varying amounts. The decrease in precipitated counts from the labeled substrate is proportional to the amount of substrate in the added sample.

Fluorescence Activated Cell Sorting (FACS):

This method involves detection of a substrate in situ in cells by substrate specific antibodies. The substrate specific antibodies are linked to fluorophores. Detection is by means of a cell sorting machine which reads the wavelength of light emitted from each cell as it passes through a light beam. This method may employ two or more antibodies simultaneously.

Immunohistochemical Analysis:

This method involves detection of a substrate in situ in fixed cells by substrate specific antibodies. The substrate specific antibodies may be enzyme linked or linked to fluorophores. Detection is by microscopy and subjective or automatic evaluation. If enzyme linked antibodies are employed, a colorimetric reaction may be required. It will be appreciated that immunohistochemistry is often followed by counterstaining of the cell nuclei using for example Hematoxyline or Giemsa stain.

In Situ Activity Assay:

According to this method, a chromogenic substrate is applied on the cells containing an active enzyme and the enzyme catalyzes a reaction in which the substrate is decomposed to produce a chromogenic product visible by a light or a fluorescent microscope.

In Vitro Activity Assays:

In these methods the activity of a particular enzyme is measured in a protein mixture extracted from the cells. The activity can be measured in a spectrophotometer well using colorimetric methods or can be measured in a non-denaturing acrylamide gel (i.e., activity gel). Following electrophoresis the gel is soaked in a solution containing a substrate and colorimetric reagents. The resulting stained band corresponds to the enzymatic activity of the protein of interest. If well calibrated and within the linear range of response, the amount of enzyme present in the sample is proportional to the amount of color produced. An enzyme standard is generally employed to improve quantitative accuracy.

TSPO Binding Assay— is described in Example 1 of the Examples section.

Exemplary antibodies and assays that may be used to detect the polypeptide markers of the present invention are further described in the Examples section herein below.

Other saliva markers contemplated for use in combination with the above described markers, include reactive nitrogen species (RNS) markers, reactive oxygen species (ROS) markers and antioxidant markers. RNS and ROS are principal induces of OSCC and the salivary antioxidant system comprises pivotal anticancer enzymes such as glutathione S-transferase (GST), which catalyzes glutathione conjugation to the carcinogen electrophilic epoxide intermediates to protect against DNA damage and adduct formation.

As used herein, the phrase "reactive nitrogen species marker" refers to a molecule whose presence correlates with the reactive nitrogen species in the saliva. The reactive nitrogen species marker may be a reactive nitrogen species itself or a molecule that is regulated by a reactive nitrogen species. RNS is a nitrogen containing molecule, highly reactive due to the presence of unpaired valence shell electrons. Examples of reactive nitrogen species markers include nitrates, nitrites and nitric oxide. Methods of detecting reactive nitrogen species markers are described in Example 2 of the Examples section herein below.

As used herein, the phrase "reactive oxygen species (ROS) marker" refers to a molecule whose presence correlates with the reactive oxygen species in the saliva. The reactive nitrogen species marker may be a reactive oxygen species itself or a molecule that is regulated by a reactive oxygen species. ROS refers to both inorganic and organic oxygen containing molecules, highly reactive due to the presence of unpaired valence shell electrons, formed as a natural byproduct of the normal metabolism of oxygen. Examples of reactive oxygen species include but are not limited to superoxide radicals ($O_2$), hydroxyl radicals (OH), and hydrogen peroxide ($H_2O_2$). Methods of detecting reactive oxygen species markers are described in Example 2 of the Examples section herein below and further described in the Invitrogen handbook section 18.2, "Generating and Detecting Reactive Oxygen Species".

The phrase "antioxidant marker" as used herein, refers to a molecule whose presence correlates with the amount of antioxidant in the saliva. The antioxidant marker may be an antioxidant itself or a molecule that is regulated by an antioxidant. Examples of antioxidant markers include, but are not limited to Glutathione S-transferase (GST), Superoxide dismutase (SOD), 8-Hydroxy-2'-deoxyguanosine (8OHDG), Uric acid, ferrylmyoglobin and peroxidase. Methods of detecting antioxidant markers are described in Example 2 of the Examples section herein below.

As mentioned, the method of the present invention comprises measuring any of the above described marker(s) and comparing the measurement with an unaffected (saliva or tissue, dependent on the marker used) sample wherein a change in the amount of the salivary component or feature is indicative of the cancer.

As used herein, the phrase "unaffected saliva sample" refers to a saliva sample taken from a healthy subject or from the same subject prior to the onset of the cancer. Since saliva characteristics and quantities of saliva components depend on, amongst other things, species and age, it is preferable that the non-cancerous control saliva come from a subject of the same species, age and from the same sub-population (e.g. smoker/nonsmoker). Alternatively, control data may be taken from databases and literature. It will be appreciated that the control sample may also be taken from the diseased subject at a particular time-point, in order to analyze the progression of the disease.

The term "change" as used herein refers to an up-regulation (e.g., MMP-9, carbonyls, KI67, LDH, Cyclin D1) or a down-regulation (e.g., OGG-1, p-Src, Maspin).

It will be appreciated that the tools necessary for detecting the salivary markers of the present invention may be provided as a kit, such as an FDA-approved kit, which may contain one or more unit dosage form containing the active ingredient for detection of a salivary marker of the present invention.

Alternatively, the kit may comprise means for collecting the sample and specific antibodies packaged separately.

The kit may be accompanied by instructions for use. The kit may also be accompanied by a notice in a form prescribed by a governmental agency regulating the manufacture, use, or sale of pharmaceuticals, which notice is reflective of approval by the agency of the form of the compositions for human or veterinary administration. Such notice, for example, may include labeling approved by the U.S. Food and Drug Administration.

For example, for detection of salivary markers, the kit may be comprised in a device such as a dipstick or a cartridge, (optionally comprised in a housing) which the subject places into the mouth and detects a change in a salivary component. The device may comprise any agent capable of specifically detecting the salivary markers of the present invention. For example, the device may comprise one or a combination of monoclonal and polyclonal antibody reagents and an indicator for detecting binding. Antibody supports are known in the art. In an embodiment of this invention, antibody supports are absorbent pads to which the antibodies are removably or fixedly attached.

According to a preferred embodiment, the device is a lateral flow device comprising inlet means for flowing saliva into contact with the agents capable of detecting the saliva markers of the present invention. The test device can also include a flow control means for assuring that the test is properly operating. Such flow control means can include control antigens bound to a support which capture detection antibodies as a means of confirming proper flow of sample fluid through the test device. Alternatively, the flow control means can include capture antibodies in the control region which capture the detection antibodies, again indicating that proper flow is taking place within the device.

In one embodiment, the kit comprises a monoclonal biomarker colored conjugate and polyclonal anti-biomarker coated on a membrane test area. By capillary action, the saliva sample migrates over the test area and reacts with the impregnated reagents to form visible colored bands in the test window. The presence of the biomarker in concentrations above normal will result in the formation of a distinct colored band in the test area thus indicating a positive result for the caner. Conversely, if no line appears in the test area, the test is negative.

Reference is now made to FIG. 10, which is a schematic illustration of a device 10, according to various exemplary embodiments of the present invention. Device 10 comprises a solid support 12, which is comprised on one end of an inlet 14 comprising an absorbent material able to draw saliva by capillary. Examples of hydrophylic capillary materials that may be used in accordance with the present invention are paper, cellulose powder cotton or other cellulose derivatives, hydrophylic polymers, polysaccharides or polyols, kaolin, titanium dioxide, barium sulfate, and diatomaceous earth. One side of the inlet 14 is placed in the mouth. The other side of the inlet 14 is attached to a test area 16. The test area 16 is comprised of a membrane or filter which binds agent 18, made from materials such as nitrocellulose, nylon, Immunodyne, Biodyne, activated paper with pore size ranging from 0.45 to 12 µm, Agent 18 may be any agent that is capable of detecting the markers of the present invention. In one embodiment agent 18 is an antibody. It will be appreciated that more than one agent 18 may be fixed on the test area 16. The number of agents 18 fixed on the test area 16 will vary according to the number of markers to be detected.

A flow indicator 20 may be present on the test area 16 and may be, for instance, a pH indicator compound able to change color when wetted by saliva, for example bromophenol blue.

The test area 16 and the absorbent material of the inlet 14 may be sealed in a housing 22 wherein the upper part of the inlet 14 is left free. The device of the invention can be shaped in several forms suited for the intended use, for instance as a stick, small tube, strip-supported on plastic material, paper or the like.

Once the diagnosis is made, the subject is informed of the diagnosis (e.g., of oral cancer or oral pharyngeal cancer) or prognosis and optionally advised of the course of action. This may include treating the cancer using methods which are well known in the art or continued monitoring at the physician's discretion.

When necessary, the above results are corroborated using methods and means which are well known in the art (oral biopsy accompanied by histopathology, PGD-PET, CAT or CT scan, oral examination, dental X-ray, head X-ray, ultrasonography).

It is expected that during the life of a patent maturing from this application many relevant markers and assays will be developed and the scope of the terms described herein is intended to include all such new technologies a priori.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683, 202; 4,801,531; 5,192,659 and 5,272,057; "Cell Biology: A Laboratory Handbook", Volumes I-III Cellis, J. E., ed.

(1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

MATERIALS AND EXPERIMENTAL PROCEDURES

Patients and Study Design

The data analyzed in the current study relates to 19 patients (no exclusion criteria were employed) who were diagnosed with tongue cancer. This study group included 12 females and 7 males, mean age 66±4 (range 27-86), who were compared to a control group with a similar age and gender distribution. The data obtained included staging (according to the TNM criteria), histological grading, depth of the tumor, maximal tumor diameter, localization at the base vs. mobile part of the tongue and the patients, smoking habit, age and gender. Analysis of salivary levels of 8-oxoguanine DNA glycosylase termed herein, OGG1 (UniProtKB/Swiss-Prot: OGG1 HUMAN, 015527), serpin peptidase inhibitor, Glade B (ovalbumin), member 5, termed herein, Maspin (UniProtKB/Swiss-Prot: SPB5_HUMAN, P36952), phospho-Src, Cyclin D1, termed herein CycD1 (CCD1, UniProtKB/Swiss-Prot: CCND1 HUMAN, P24385), Proliferation related Ki67 antigen (Ki67, UniProtKB/Swiss-Prot: KI67 HUMAN, P46013) and matrix metallopeptidase 9 (termed herein, MMP-9 UniProtKB/Swiss-Prot: MMP9 HUMAN, P14780) was performed. Additional markers tested included Lactate dehydrogenase, termed herein LDH and total carbonyl levels. All these were measured in saliva, which was collected as described below, shortly prior to the administration of the definitive curative treatment. This included surgical removal of the primary tongue tumor, neck dissection and, in most cases, post-operative adjuvant radiotherapy.

Saliva Collection

Whole saliva was collected shortly prior to the administration of definitive therapy under non-stimulatory conditions in a quiet room between 8 A.M. and noon, at least one hour after eating. Patients were asked to generate saliva and to spit into a wide test tube for ten minutes as previously described (Nagler and Hershkovich). Following collection, the saliva was immediately centrifuged at 800 g at 4° C. for 10 min to remove squamous cells and cell debris.

Immunoreactivity Assay for Salivary Markers

Saliva samples were centrifuged (800×g, 10 min, 4° C.), and the pellets were suspended in 150 µl of lysis buffer (45 mM HEPES, 0.4 M KCl, 1 mM EDTA, 10% glycerol, pH 7.8). Following 30 min incubation at room temperature the samples were centrifuged (11,000×g, 10 min, 4° C.). Protein concentration in the supernatants was determined. A volume containing 50 ng of protein was transferred to a 1.5 ml vial and all samples were brought to the same volume of 500 µl with the addition of PBS. The solutions were mixed well and 100 µl of each sample was added to ELISA-plate wells (96 well nunc-immunoplate; Thermo Fisher Scientific). The plate was covered and stored over-night at 4° C. The next day, each well was washed three times with 100 µl PBS-Tween solution (PBS-T, PBS containing 0.05% Tween 20) and a volume of 100 µl of 1% BSA PBS-T blocking solution (PBS containing 0.05% Tween 20 and 1% BSA) was added to each well. After 1 h incubation at room temperature, 100 µl of primary antibody was added to each well. Antibody details are described below. Following 2 h incubation at room temperature, the plate was washed as described above and a volume of 100 µl of secondary antibody was added to each well. Following 2 h incubation at room temperature the plate was washed as described above. In order to achieve color development, 100 µl of 3,3',5,5'-tetramethylbenzidine solution (TMB) (Southern Biotech) were added to each well. After 1-2 min, 100 µl of stopping reagent were added to each well (10% sulphuric acid). Absorbencies of the samples, representing the levels of the specific proteins examined, were measured at the wavelength 450 nm directly after the addition of the stopping reagent, using a Zenith 200 ELISA reader (Anthos, Eugendorf, Austria).

Antibodies

MMP-9—monoclonal rabbit anti human antibody (1:1000; Sigma-Aldrich, Saint Louis, Mo., USA); OGG1—monoclonal rabbit anti human antibody (1:10000; Alpha Diagnostic International, San Antonio, Tex., USA); p-SRC—monoclonal rabbit anti human antibody (1:1000; Sigma-Aldrich, Saint Louis, Mo., USA); Ki67—monoclonal rabbit anti human antibody (1:1000; Acris Antibodies, Herford, Germany); Maspin—monoclonal rabbit anti human antibody (1:1000; Sigma-Aldrich, Saint Louis, Mo., USA); CycD1—polyclonal rabbit anti human antibody (1:500; Sigma-Aldrich, Saint Louis, Mo., USA). For all assays a peroxidase-conjugated goat anti rabbit secondary antibody was used (1:5000; Jackson Immunoresearch, West Grove, Pa., USA).

LDH Activity

For measurement of LDH activity saliva samples were diluted by 10 using double distilled water. The activity of LDH was determined by kinetic-spectrophotometry using a commercial kit (Siemens Healthcare Diagnostics, Deerfield, Ill., USA) and a Dimension RXL analyzer (Siemens Healthcare Diagnostics, Deerfield, Ill., USA).

Detection of Protein Oxidation (Protein Carbonyl Assay)

An enzyme-linked immunosorbent assay (ELISA) colorimetric test kit (Cayman Chemical, New Zealand) was used to quantitatively measure the products of protein oxidation (carbonyls) in pleural fluid samples. Samples were centrifuged (800×g, 10 min, 4° C.), and the pellets were suspended in 150 µl of lysis buffer (45 mM HEPES, 0.4 M KCl, 1 mM EDTA, 10% glycerol, pH 7.8). Following 30 min incubation at room temperature the samples were centrifuged (11,000×g, 10 min, 4° C.) and the supernatants were stored at −20° C. On the day of the carbonyl analysis, the supernatants were thawed and protein concentrations were determined. A volume of 20 µg was transferred to a 1.5 ml vial and all samples were brought to the same volume of 100 µl with the addition of water of high pressure liquid chromatography grade (HPLC). 0.8 volumes of ice cold 28% trichloroacetic acid (TCA) was added, mixed well, and after 10 min of incubation on ice, the tubes were centrifuged (10,000×g, 3 min, 4° C.). Supernatants were carefully aspirated without disturbing the pellet. 5 µl of EIA buffer (1 M phosphate solution containing 1% BSA, 4 M NaCl, 10 mM EDTA and 0.1% sodium azide) and 15 µl diluted 2,4-dinitrophenol (DNP) solution were added to samples according to the manufacturer's instructions. Following 45 min incubation at room temperature, 5 µl of each sample were taken to a parallel set of 1.5 ml vials containing 1 ml EIA buffer. The solutions were mixed well and 200 µl of each sample was added to ELISA-plate wells. The plate was covered and stored over-night at 4° C. The next day, the plate was washed three times with EIA buffer (250 µl per well) and 250 µl of diluted blocking solution (provided by the manufacturer) were added to each well. After 30 min incubation at room temperature, the wells were washed as described above and 200 µl of diluted anti-DNP-biotin-antibody was added to each well. The plate was incubated for 1 h at 37° C. Following incubation, the plate was washed and 200 µl of diluted streptavidin-HRP were added to each well. After 1 hour incubation at room temperature the plate was washed as described above. In order to achieve color development, 200 µl of chromatin reagent (provided by the manufacturer) were added to each well. After 5 min, 100 µl of stopping reagent were added to each well. Absorbencies of the samples were measured at the wavelength 450 nm directly after the addition of the stopping reagent, using a Zenith 200 ELISA reader (Anthos, Eugendorf, Austria). In order to quantify the absorbance values, the same procedure was performed for standard and control samples provided by the manufacturer, and a standard curve was provided.

Statistical Analysis:

Data concerning the levels of various markers were evaluated in saliva and the mean, standard deviation (STD) and standard error (SE) values were analyzed and compared with the two-sample t-test for differences in means. The criterion for statistical significance was p<0.05. The correlations between the marker levels in saliva were analyzed using the Pearson correlation analysis. A correlation matrix of estimators was used to analyze the correlation coefficients between the salivary parameters. For classification analysis, cutoff values were calculated as mean plus/minus one STD value of healthy controls. Sensitivity and specificity values were calculated as the fraction of observations, which were correctly classified.

Example 1

Expression of MMP9, OGG1, Maspin and KI67 or Combinations thereof is Correlated with OSCC Clinical Data, Staging, Pathological Grading, Dimensions, Site and Extension of the Tumors The distribution of the 19 patients according to tumor size (T) revealed that seven had T1 and eight patients had T2 tumors while only two patients had T3 and two patients had T4 tumors. That is, nearly 80% of the patients had early (small to moderate) tumors. In 13/19 (68%) of the patients there were no neck metastasis (N0) while 4 patients were diagnosed with N1 and 2 with N2. None had distant metastasis (all patients were M0). Accordingly, 68% of the patients were diagnosed with early stage tumors (1+2) while only 32% were diagnosed with advanced stages (3+4). Similarly, most of the patients (84%) were diagnosed with well- and moderately-differentiated tumors and only 3 patients were diagnosed with poorly differentiated lesions. In 16% of the patients (3/19) the tumor extended beyond the lingual region and expanded locally towards neighboring regions, as the floor of the mouth.

The mean tumor diameter at diagnosis was 3.4±0.9 cm (range 0.5-8.0 cm) and the mean depth was 3.4±0.9 mm (range 1-25 mm). Only 12.5% of the patients smoked (two of the 16 for whom this information was available). The rate of smokers in the control group was not significantly different. Only 2/19 patients had a previous pre-malignant lesion (Lichen planus) and only 1/17 patients (for whom the data was available) had other previous malignancy and none had been previously treated with radiotherapy. None of the controls was treated with radiotherapy or had a previous head and neck cancer.

Salivary Tumor Markers

Salivary tumor marker analysis revealed highly significant changes in the levels of all 6 markers analyzed (Table 1 below). Of these the following were increased in the cancer patients by 39%-246%: Ki67, CycD1, LDH, carbonyls and MMP-9 (p≤0.01). The other 3 markers were decreased in the cancer patients by 16%-29%: OGG, Maspin and p-SRC (p≤0.01).

The salivary mean (±SE) concentrations (OD values) in controls of MMP-9, Ki67, CycD1, OGG1, p-SRC and Maspin were 0.04±0, 0.37±0.23, 0.15±0.05, 0.70±0.03, 0.50±0.02, 0.67±0.03 and 0.44±0.02 respectively. Especially significant were the alterations in CycD1 (an increase by 87%, p=0.000006) and in Maspin (a decrease by 29%, p=0.007), (Table 1). The sensitivity values of the 8 analyzed markers were in the range of 58%-100% while the specificity values were in the range of 42%-100% (Table 1 below).

TABLE 1

Statistical analysis of the eight analyzed salivary biomarkers.

| Parameter | % of change (out of control) | p | Sensitivity | Specificity |
| --- | --- | --- | --- | --- |
| MMP-9 | 39% | 0.014 | 100% | 69% |
| Carbonyls | 246% | 0.012 | 90% | 80% |
| OGG1 | −16% | 0.007 | 77% | 75% |
| p-Src | −24% | 0.010 | 77% | 75% |
| Ki67 | 127% | 0.015 | 58% | 67% |
| Maspin | −29% | 0.001 | 100% | 100% |
| LDH | 86% | 0.002 | 79% | 42% |
| CycD1 | 87% | P < 0.00001 | 100% | 100% |

All markers were found to be highly significantly altered in the saliva of oral cancer patients as compared to controls. The following were calculated: percentage of change in the mean levels of each parameter, statistical significance of the change (represented by p), sensitivity and specificity values for each biomarker.

Combination Marker Analysis

Multiple significant (<−0.4 or r>0.4) correlations were demonstrated among all 8 markers, each with some of the others. The most significant correlations were demonstrated between: Maspin and CycD1 (0.89), carbonyls and CycD1 (0.79, carbonyls and Maspin (0.75) and carbonyls and Ki67 (0.72). Also quite high were the significant correlations between CycD1 and MMP-9 (0.67) and between Maspin and OGG1 (0.62), (Table 2).

TABLE 2

List of biomarkers that were found to be significantly
correlated (r - Pearson correlation coefficient;
r < –0.4 or r > 0.4 - significant correlation).

| Parameters compared | r |
|---|---|
| MMP9-CycD1 | 0.67 |
| MMP9-Carbonyls | 0.57 |
| MMP9-Ki67 | 0.48 |
| Carbonyls-OGG1 | 0.57 |
| Carbonyls-Ki67 | 0.72 |
| Carbonyls-Maspin | 0.75 |
| Carbonyls-CycD1 | 0.79 |
| Carbonyls-LDH | 0.56 |
| OGG1-Src | 0.55 |
| OGG1-Maspin | 0.62 |
| OGG1-CycD1 | 0.54 |
| OGG1-LDH | 0.42 |
| Ki67-CycD1 | 0.54 |
| Maspin-CycD1 | 0.89 |

Example 2

TSPO Levels can be Used as a Diagnostic and Prognostic Marker for OSCC

Materials and Methods

Experimental design: The in vivo part of the study was based on an analysis of 69 patients (33 males and 36 females aged 65.7±15.2 years) with tongue cancer whose archival paraffin-embedded pathological material was available for immunohistochemical staining analysis of TSPO. In 41 cases the TSPO staining levels were studied together with those of Skp2 and p27 proteins. The analysis was performed as previously described [O. Ben-Izhak, S. Akrish, S. Gan, R. M. Nagler, P27 and salivary cancer, Cancer Immunol. Immunother. 58 (2009), 469-473]. Seventeen patients were diagnosed with stage 1 disease; 27 with stage 2; 10 with stage 3; and 15 with stage 4. All patients had their tumors resected within 1-2 weeks after diagnosis, followed by radiation therapy to the head and neck region for patients at stages 2-4, with a mean dose of 60 Gy. The study protocol was approved by the Institutional Review Board. Clinical data included histopathological grading, tumor-node-metastasis (TNM) staging, and status at the end of the study (alive or deceased).

In the in vitro part of the study TSPO binding and expression was analyzed in the oral cancer cell lines, SCC-25 and SCC-15, purchased from the American Type Culture Collection (ATCC, Manassas, Va., USA). In addition, the cellular fraction of saliva from oral cancer patients was analyzed, as well as from a group of cigarette smokers, and their control groups matching in age and gender. For the oral cancer patient's analysis, whole saliva was collected from a group of otherwise-healthy, consenting oral cancer patients who were compared to a control group of healthy individuals who matched in age and gender. None of the patients had a history of smoking, none of alcohol-drinking, and none had a history of oral pre-malignant lesions or any other oral disease. All cancer lesions were located at the lateral aspect of the mobile tongue. The saliva was collected prior to the administration of the therapy, and frozen at –70° C. before further processing and analysis.

For in vivo salivary analysis of a group of heavy smokers (over 20 cigarettes daily for at least 10 years) all smokers were asked to schedule the smoking of one of their cigarettes immediately prior to saliva collection, to reduce potential variability that may otherwise be introduced by the various time spans between exposure to cigarette smoke and saliva collections. The smokers were compared with a control group of healthy non-smoking individuals. Following collection and storage, the salivary samples were subjected to cell viability observations, TSPO binding assays, Western blot analysis, and protein level determination as previously described. It has been reported previously that saliva may contain various types of cells, including exfoliated epithelial mucosal cells. An in vitro salivary analysis was conducted in which the cellular fractions of saliva samples collected from healthy non-smoking volunteers (age range 20-65 years; 60% females and 40% males) were subjected to TSPO binding assay following exposure to cigarette smoke (14 mg tar and 0.9 mg nicotine per cigarette), as previously described [A. Z. Reznick, O. Hershkovich, R. M. Nagler, Saliva—a pivotal player in the pathogenesis of oropharyngeal cancer, Br. J. Cancer 91 (2004), 111-118]. Briefly, a cigarette was combined with a vacuum system to enable the inhalation of gas-phase cigarette smoke into a sealed apparatus containing the salivary samples (whole saliva) [A. Z. Reznick supra]. Previous studies have shown, by measuring the $NO_2$— concentrations in the media, that the time of exposure to the smoke correlates directly with the level of exposure to cigarette smoke. Using the same system the present inventors also exposed oral cancer cell lines to cigarette smoke. Using these various models allowed studying oral cancer both at the tissue level (specimens of tumors) and at the cellular level (cells in saliva and oral cancer cell lines in cell culture medium).

Immunohistochemical Analysis and Western Blot:

The preparation and specificity of the antiserum against TSPO was described previously [17, 18, 20]. This antiserum was used for the immunohistochemistry and Western blot analysis of the present study. Western blot analysis with this antiserum was performed as described in detail previously [17, 18, 20]. Labeling of β-actin was used as a loading control. Labeling for the 32 kDA voltage dependent anion channel (VDAC) was done as routinely performed in our laboratory [e.g. 17, 20, 27] as it is a protein closely associated with the TSPO.

For immunohistochemical staining of oral cancer specimens and control tissue, five micron sections were deparaffinized with xylene and rehydrated in a series of ethanol. Endogenous peroxidase was blocked by 3% hydrogen peroxide in methanol for 20 minutes. For epitope retrieval, slides were heated in a microwave oven at 92° C. for 20 minutes in a Tris-EDTA-buffer pH 8.0. After cooling, slides were washed in distilled water and then in phosphate-buffered saline (pH 7.4). Slides were incubated overnight at 4° C. with the primary antiserum directed against TSPO diluted 1:100. Staining was completed with a Histostain-Plus kit (Zymed laboratories, CA). Color reaction product was developed with aminoethylcarbazole as the chromogen. All sections were counterstained with hematoxylin, dehydrated, and cover slipped. Incubations with phosphate-buffered saline containing 1% bovine serum albumin instead of the primary antibody were used as negative controls. Skp2 and p27 antisera were applied with similar immunostaining procedures, as described previously [21, 34].

Staining intensity was examined microscopically, double blind, as neither the person examining the sections nor the person providing the sections to the examiner knew the patient origin of the samples. Weak cytoplasmic staining intensity for TSPO of tumor cells was graded <1 (weak). Weak staining meant that less than 50% of tumor cells were stained. Moderate to strong cytoplasmic staining of tumor cells was graded >1 (moderate-strong). In all cases of moderate to strong staining for TSPO more than 50% of tumor cells were stained. Skp2 and p27 staining intensity was determined as described previously i.e. at least 500 tumor cell nuclei were counted and from this population the percentage of Skp2 and p27 positive cells was calculated [21, 34].

Cell Viability:

Cell viability was determined in saliva samples using the Trypan Blue exclusion test. Following treatment, saliva samples were centrifuged at 800×g for 10 minutes and the pellet containing the cellular fraction was suspended in phosphate buffered saline (PBS). Cell counting was performed using an inverted microscope and a hemocytometer. Both viable and non-viable cells were counted and the percentage of viable cells was calculated from the total number of cells.

Mitochondrial Transmembrane Potential Analysis:

The specific stain JC-1 (5,5',6,6'-tetrachloro-1,1',3,3'-tetraethylbenzimidazolylcarbocyanine iodide) was used to assay changes in the $\Delta\psi_m$ following exposure oral cancer cell lines to cigarette smoke, as described in detail previously [17, 20, 35]. Briefly, samples of confluent cells were collected and centrifuged at 1200×g for 10 min. Cell pellets were re-suspended in 1 μg/ml JC-1 solution in PBS and incubated at 37° C. for 30 min in the dark. After incubation, the cells were centrifuged at 1200×g for 10 min, and re-suspended in 0.5 ml PBS. Then, the cell suspensions were transferred into 5 ml FALCON® FACS tubes and analyzed with the flow cytometer using CellQuest software.

TSPO Binding Analysis of Saliva and Oral Cancer Cells:

Assays of [$^3$H] PK 11195 binding to membranes of the SCC-15 and SCC-25 cells for Scatchard analysis were conducted, according to methods described previously [14, 16, 25]. The reaction mixture contained 400 μl of the homogenized samples and 25 μl of [$^3$H]PK 11195 (final concentration of 0.2-6 nM), in the absence (total binding) or in the presence (nonspecific binding) of 10 μM unlabeled PK 11195. After 80 minute incubation at 4° C., the samples were filtered through Whatman CF/C filters using a vacuum system, washed three times with 4 ml of 5 mM ice cold phosphate buffer and placed in vials containing 4 ml of CytoScint™ (MP Biomedicals, Costa Mesa, Calif.). Radioactivity was counted after 12 hours with a liquid scintillation analyzer. Specific binding was obtained by subtracting non-specific binding from total binding. The maximal binding capacity ($B_{max}$) and equilibrium dissociation constant ($K_d$), were calculated from the saturation curve of [$^3$H]PK 11195 binding, using Scatchard analysis.

For binding analysis of the cellular fraction of saliva, saliva samples were thawed and immediately centrifuged (800×g, 10 min, 4° C.). The pellet, containing cells present in the saliva, was suspended in ice cold PBS, and then homogenized using a Kinematika Polytron (Luzerne, Switzerland) (setting 6) for 10 seconds. Total protein amount was determined, according to Bradford et al. [24]. TSPO binding assays of the saliva were conducted at concentrations of 6 nM and 12 nM of [$^3$H] PK 11195.

Statistical Analysis:

For categorical variables, frequencies and percentages were calculated. Distributions for categorical variables were compared and analyzed by the Fisher-Irwin exact test (small sample). For continuous variables, ranges, means, standard deviation, and standard error were calculated. The results of continuous variables between subgroups of patients were compared and analyzed by one way analysis of variance. The "Kaplan Meier estimate" was used to calculate the probability of survival rates as a function of time. The "Log Rank test" was used to compare between survival curves. P<0.05 was taken as indicating statistically significant differences.

Results

Tissue section analysis in which TSPO staining was effected as described above. Of the 69 oral cancer patients analyzed, 12 (18%) stained negatively (=O) for TSPO while the other 57 (82%) stained positively. The TSPO-positive group was further categorized according to the intensity of staining: weak staining (≤1) was found in 52% (36/69) of the specimens and profound staining (>1) in 30% (21/69). The TSPO staining was cytoplasmic and slightly granular in the tumor tissue while the adjacent, normal-looking tissue was not stained by the anti-TSPO antibody, thus serving as internal controls (FIGS. 1A-B). TSPO immunostaining was not significantly different in males and females nor significantly altered by age. Neither did the TSPO level significantly correlate with the grading or with the T, N or M values.

Prognostic Value of TSPO for Oral Cancer

In order to determine the prognostic value of TSPO for tongue cancer patients, their cumulative survival was analyzed according to TSPO expression levels. The intensity of TSPO tissue staining inversely correlated with patient survival rate. Thus, 65% of the patients negative for TSPO were still alive at 60 months, compared with 57% and 7% of the patients with low (1) and high (2) TSPO levels, respectively (p=0.0001), (FIG. 2).

TSPO staining level correlated with those of Skp2 and p27. The mean Skp2 staining level of the TSPO positive (>0) specimens was significantly lower than that of the TSPO negative specimens (=O), 14.5±2.1% (n=32) vs 21.5±4.7% (n=7) respectively (p=0.05), (Table 3A, below). In contrast, the mean p27 staining level of the TSPO positive specimens was significantly higher than that of the TSPO negative specimens, 39±2.3% (n=34) vs. 27±4.2% (n=7) respectively (p=0.03), (Table 3B, below).

TABLE 3A

Skp2 by TSPO level

| TSPO level/Skp2(%) | 0 | >0 |
|---|---|---|
| Patients | 7 | 32 |
| Range | [3-40] | [1-48] |
| Mean | 21.5 | 14.51 |
| SER | 4.77 | 2.10 |

(p = 0.05)

TABLE 3B p27 by TSPO level

| TSPO level/p27 (%) | 0 | >0 |
|---|---|---|
| Patients | 7 | 34 |
| Range | [12.5-37.5] | [12.5-62.5] |
| Mean | 27 | 39 |
| STD | 4.2 | 2.3 |

(p = 0.035)

Tables 3A-B: Correlations between TSPO and Skp2 (A) and TSPO and p27 (B) staining levels. When the TSPO staining level was >0, the Skp2 staining level was significantly reduced (p = 0.05) and that of the p27 was significantly increased (p = 0.035), as compared to the situation where the TSPO staining level was =0.

The results shown in the FIG. 2 are also represented by Table 4, below.

TABLE 4

| TSPO | Stage | Dead/Live | Survival (months) |
|---|---|---|---|
| 0 | 4 | 0 | 60 |
| 0 | 4 | 0 | 60 |
| 0 | 4 | 1 | 13 |

TABLE 4-continued

| TSPO | Stage | Dead/Live | Survival (months) |
|---|---|---|---|
| 0 | 3 | 1 | 50 |
| 2 | 2 | 1 | 9 |
| 2 | 2 | 1 | 39 |
| 2 | 2 | 1 | 12 |
| 2 | 1 | 0 | 60 |
| 2 | 2 | 1 | 14 |
| 2 | 2 | 1 | 12 |
| 1.5 | 1 | 1 | 20 |
| 2 | 1 | 1 | 26 |
| 2 | 2 | 1 | 19 |
| 2 | 1 | 1 | 45 |

TSPO in the SCC-25 and SCC-15 Cells:

Western blots were carried out to determine whether TSPO is present in SCC-25 and SCC-15 cells. TSPO indeed are expressed in these human oral cancer cells. A representative Western blot of SCC-25 cells is presented in FIG. 3.

TSPO Binding Characteristics of [$^3$H]PK 11195 in the SCC-25 and SCC-15 Oral Cancer Cell Lines:

Binding assays with [$^3$H]PK 11195 showed B. and $K_d$ values for the SCC-25 cells of 3133±643 fmoles/mg protein and 5.7±2.0 nM, respectively (mean±SD, n=7). The $B_{max}$ and $K_d$ values of the SCC-15 cells were 6956±549 fmoles/mg protein and 5.9±4.6 nM, respectively (mean±SD, n=16). Non-specific binding of [$^3$H]PK 11195 to human oral cancer cells was one third of the total binding. Representative Scatchard analysis of saturation curves of [$^3$H]PK 11195 specific binding to TSPO in human oral cancer cell lines SCC-25 and SCC-15 is presented in FIGS. 4A-B.

TSPO Binding and Protein Concentration Following Exposure of SCC-25 and SCC-15 Cells to Cigarette Smoke:

With binding assays of SCC-25 cells that were exposed to CS for 90 minutes, using [$^3$H]PK 11195 as a radioligand (final concentrations 3 nM and 6 nM) a significant decrease of 72% was found in TSPO binding at the concentration of 3 nM [$^3$H]PK 11195 in the CS-exposed cells, as compared to controls (n=6; p=0.01; data not shown). Similarly, the mean TSPO binding at a final concentration of 6 nM was lower by 56% in the CS-exposed cells (n=6; p=0.05; data not shown). Using a concentration of 3 nM [$^3$H]PK 11195 in CS-exposed SCC-15 cells, a significant decrease of 64% in TSPO binding as compared to controls (data not shown) was also found. Total protein concentrations in SCC-25 and SCC-15 cells exposed to cigarette smoke (CS) for 90 minutes did not differ from controls, as measured by the method of Bradford et al. [24].

Collapse of the Mitochondrial Transmembrane Potential in SCC-25 Cells Exposed to Cigarette Smoke:

The mitochondrial potential stability assays as assayed in SCC-25 cells showed that cigarette smoke caused collapse of the mitochondrial membrane potential ($\Delta\psi_m$) in 80% of the cells, which present a significant increase as compared to control (FIG. 5). Collapse of the $\Delta\psi_m$ can lead to cell death, including apoptosis [17,20].

TSPO Binding, Cell Viability, and Total Protein in the Cellular Fraction of Saliva of Heavy Smokers:

Similar to the effects of CS on the TSPO binding in the oral cancer cell lines, the cellular fraction of saliva from heavy smokers showed that the mean±SE TSPO binding with the [$^3$H]PK 11195 ligand (at a final concentration of 6 nM) was reduced significantly by 53% (9 smokers), as compared to the control group (16 non-smokers) (p<0.05) (FIG. 6A). Western blot analyses of TSPO, VDAC and β actin proteins in the cellular fraction of saliva from non-smoking individuals and smoking individuals, revealed a lower expression of the TSPO and VDAC proteins in heavy smokers (FIG. 6B). The mean±SE percentage values of viable salivary cells were found to be similar in both groups, with 36±4% in control saliva (16 non-smokers) and 37±4% in smokers saliva (6 smokers). Also the mean±SE of total protein concentration in saliva of non-smoking controls (16 non-smokers) and heavy smokers (9 smokers) were similar, i.e. 0.31±0.08 mg/ml and 0.44±0.16 mg/ml respectively.

In Vitro Analysis of TSPO Binding, Cell Viability, and Total Protein Levels in Saliva Exposed to CS:

Saliva samples which had been collected from healthy non-smoking volunteers were exposed to CS in vitro and then the cellular fraction subjected to TSPO binding analysis. The binding analysis with a single [$^3$H]PK 11195 (6 nM final concentration), in control and CS-exposed saliva revealed a significant 30% reduction of the TSPO binding (n=34, p<0.001) in response to CS-exposure, compared to sham controls (FIG. 7). Cigarette smoke did not appear to affect cell viability in saliva. The mean percentage values of viable cells were found to be similar in both groups, with 32.0±3.8% in control saliva (n=25) and 36.0±3.5% (n=25) in cigarette smoke-exposed saliva. The mean total protein concentrations in the cellular fractions from the control and the cigarette smoke-exposed samples were similar (data not shown).

TSPO Binding, Cell Viability, and Total Protein Levels in Saliva of Oral Cancer Patients:

Two separate binding experiments were conducted on saliva samples of oral cancer patients and healthy controls, using [$^3$H]PK 11195 as a radioligand. In the first experiment two concentrations of [$^3$H]PK 11195 (6 nM and 12 nM) were used, and in the second experiment we used 6 nM only. In the first experiment (FIG. 8) 13 salivary samples of oral cancer patients were compared with 6 salivary samples of controls, and found a significant 38% decrease in TSPO binding at the concentration of 6 nM [$^3$H]PK 11195 (p<0.05) in the cellular fraction of saliva from oral cancer patients, as compared to controls. Similarly, the mean TSPO binding at a final concentration of 12 nM was significantly lower by 41% in the cancer patients (p<0.05) (FIG. 8). In the second experiment, using 6 nM final concentration of [$^3$H]PK 11195, the decrease in TSPO binding in the cellular fraction from saliva of oral cancer patients was 40% (n=12 for healthy controls, n=7 for oral cancer patients, p<0.05).

Viability assays with Trypan blue showed that the mean±SE percentage values of viable cells were similar in both groups, with 48±7% in saliva of controls (n=16) and 40±4% in saliva of oral cancer patients (n=7). Also the mean±SE total protein concentration [24] in the cellular fraction of saliva from healthy controls (n=35) and oral cancer patients (n=9) were similar (0.32±0.05 mg/ml and 0.35±0.08 mg/ml, respectively).

Discussion

The present results indicate for the first time that increased TSPO levels in oral cancer tissue may be correlated with oral cancer mortality prognosis. On the other hand, reductions in TSPO binding in the cellular fraction of saliva in the oral cavity may contribute to the occurrence of cancer. This role of salivary TSPO may be based on induced reductions in the TSPO normal binding and/or protein expression rendered by inborn defects or by a later exposure to carcinogens such as those contained in cigarette smoke (FIG. 9). Thus, our studies suggest that TSPO malfunction may contribute to carcinogenesis, implying that the TSPO may be targeted as a venue for treatment of oral cancer. More studies correlating TSPO functions with oral cancer prognosis and diagnosis are needed. In particular, causal relationships need to be established in this area.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

REFERENCES

[1] A. Z. Reznick, O. Hershkovich, R. M. Nagler, Saliva—a pivotal player in the pathogenesis of oropharyngeal cancer, Br. J. Cancer 91 (2004), 111-118.

[2] S. Kantola, M. Parikka, K. Jokinen, K. Hyrynkangs, Y. Soini, O. P. Alho, T. Salo, Prognostic factors in tongue cancer—relative importance of demographic, clinical and histopathological factors, Br. J. Cancer 83 (2000), 614-619.

[3] J. N. Myers, T. Elkins, D. Roberts, R. M. Byers, Squamous cell carcinoma of the tongue in young adults: increasing incidence and factors that predict treatment outcomes, Otolaryngol. Head Neck Surg. 122 (2000), 44-51.

[4] K. C. Ribeiro, L. P. Kowalski, M. R. Latorre, Impact of comorbidity, symptoms, and patients' characteristics on the prognosis of oral carcinomas, Arch. Otolaryngol. Head Neck Surg. 126 (2000), 1079-1085.

[5] Braestrup C, Squires RF. Specific benzodiazepine receptors in rat brain characterized by high-affinity (3H)diazepam binding. Proc Natl Acad Sci USA. 74 (1977), 3805-3809.

[6] M. Gavish, I. Bachman, R. Shoukrun, Y. Katz, L. Veenman, G. Weisinger, A. Weizman, Enigma of the peripheral benzodiazepine receptor, Pharmacol. Rev. 51 (1999), 629-650.

[7] L. Veenman, M. Gavish, The peripheral-type benzodiazepine receptor and the cardiovascular system: implications for drug development, Pharmacol. Therap. 110 (2006), 503-524.

[8] Y. Katz, G. Ben-Baruch, Y. Kloog, J. Menczer, M. Gavish, Increased density of peripheral benzodiazepine-binding sites in ovarian carcinomas as compared with benign ovarian tumours and normal ovaries, Clin. Sci. (Lond.) 78 (1990), 155-158.

[9] Y. Katz, A. Eitan, M. Gavish, Increase in peripheral benzodiazepine binding sites in colonic adenocarcinoma, Oncology 47 (1990), 139-142.

[10] K. Maaser, M. Hopfner, A. Jansen, G. Weisinger, M. Gavish, A. P. Kozikowski, A. Weizman, P. Carayon, E. O. Riecken, M. Zeitz, H. Scheriibl, Specific ligands of the peripheral benzodiazepine receptor induce apoptosis and cell cycle arrest in human colorectal cancer cells, Br. J. Cancer 85 (2001), 1771-1780.

[11] K. Maaser, P. Grabowski, A. P. Sutter, A. Krahn, B. Heine, H. Stein, H. Buhr, M. Zeitz, H. Scherübl, Up-regulation of the peripheral benzodiazepine receptor during human colorectal carcinogenesis and tumor spread, Clin. Cancer Res. 11 (2005), 1751-1756.

[12] Z. Han, R. S. Slack, W. Li, V. Papadopoulos, Expression of peripheral benzodiazepine receptor (PBR) in human tumors: relationship to breast, colorectal, and prostate tumor progression, J. Recept. Signal Transduct. Res. 23 (2003), 225-238.

[13] S. Galiègue, P. Casellas, A. Kramar, N. Tinel, J. Simony-Lafontaine, Immunohistochemical assessment of the peripheral benzodiazepine receptor in breast cancer and its relationship with survival, Clin. Cancer Res. 10 (2004), 2058-2064.

[14] L. Veenman, E. Levin, G. Weisinger, S. Leschiner, I. Spanier, S. H. Snyder, A. Weizman, M. Gavish, Peripheral-type benzodiazepine receptor density and in vitro tumorigenicity of glioma cell lines, Biochem. Pharmacol. 68 (2004), 689-698.

[15] G. Weisinger, E. Kelly-Hershkovitz, L. Veenman, I. Spanier, S. Leschiner, M. Gavish, Peripheral benzodiazepine receptor antisense knockout increases tumorigenicity of MA-10 Leydig cells in vivo and in vitro, Biochemistry 43 (2004), 12315-12321.

[16] E. Levin, A. Premkumar, L. Veenman, W. Kugler, S. Leschiner, I. Spanier, G. Weisinger, M. Lakomek, A. Weizman, S. H. Snyder, G. W. Pasternak, M. Gavish, The peripheral-type benzodiazepine receptor and tumorigenicity: isoquinoline binding protein (IBP) antisense knockdown in the C6 glioma cell line, Biochemistry 44 (2005), 9924-9935.

[17] W. Kugler, L. Veenman, Y. Shandalov, S. Leschiner, I. Spanier, M. Lakomek, M. Gavish, Ligands of the mitochondrial 18 kDa translocator protein attenuate apoptosis of human glioblastoma cells exposed to erucylphosphohomocholine, Cell. Oncol. 30 (2008), 435-450.

[18] R. Shoukrun, L. Veenman, Y. Shandalov, S. Leschiner, I. Spanier, R. Karry, Y. Katz, G. Weisinger, A. Weizman, M. Gavish, The 18-kDa translocator protein, formerly known as the peripheral-type benzodiazepine receptor, confers proapoptotic and antineoplastic effects in a human colorectal cancer cell line, Pharmacogenet. Genomics 18 (2008), 977-988.

[19] L. Veenman, Y. Shandalov, M. Gavish, VDAC activation by the 18 kDa translocator protein (TSPO), implications for apoptosis, J. Bioenerg. Biomembr. 40 (2008), 199-205.

[20] S. Zeno, M. Zaaroor, S. Leschiner, L. Veenman, M. Gavish, CoCl(2) induces apoptosis via the 18 kDa translocator protein in U118MG human glioblastoma cells. Biochemistry. 48 (2009) 4652-4661.

[21] O. Ben-Izhak, S. Akrish, S. Gan, R. M. Nagler, P27 and salivary cancer, Cancer Immunol. Immunother. 58 (2009), 469-473.

[22] T. Shpitzer, G, Bahar, R. Feinmesser, R M Nagler, A comprehensive salivary analysis for oral cancer diagnosis. J. Cancer Res. Clin. Oncol. 133(9) (2007), 613-617.

[23] A. Z. Reznick, I. Klein, J. P. Eiserich, C. E. Cross, R. M. Nagler, Inhibition of oral peroxidase activity by cigarette smoke: in vivo and in vitro studies, Free Radic. Biol. Med. 34 (2003), 377-384.

[24] M. M. Bradford, A rapid and sensitive method for the quantitation of microgram quantities of protein utilizing the principle of protein-dye binding, Anal. Biochem. 72 (1976), 248-254.

[25] M. Awad, M. Gavish, Binding of [3H]Ro5-4864 and [3H]PK 11195 to cerebral cortex and peripheral tissues of various species: species differences and heterogeneity in peripheral Benzodiazepine binding sites, J. Neurochem. 49 (1987), 1407-1414.

[26] E. Kelly-Hershkovitz, R. Weizman, I. Spanier, S. Leschiner, M. Lahav, G. Weisinger, M. Gavish, Effects of peripheral-type benzodiazepine receptor antisense knock-

[27] L. Veenman, S. Leschiner, I. Spanier, G. Weisinger, A. Weizman, M. Gavish, PK 11195 attenuates kainic acid-induced seizures and alterations in peripheral-type benzodiazepine receptor (PBR) protein components in the rat brain, J. Neurochem. 80 (2002), 917-927.

[28] R. M. Nagler, S. Lischinsky, E. Diamond, I. Klein, A. Z. Reznick, New insights into salivary lactate dehydrogenase of human subjects, J. Lab. Clin. Med. 137 (2001), 363-369.

[29] G. Bahar, R. Feinmesser, T. Shpitzer. A. Popovtzer, R M. Nagler, Salivary analysis in oral cancer patients: DNA and protein oxidation, reactive nitrogen species, and antioxidant profile. Cancer. 109(1) (2007), 54-59.

[30] R. Nagler, G. Bahar, T. Shpitzer, R. Feinmesser, Concomitant analysis of salivary tumor markers—a new diagnostic tool for oral cancer. Clin. Cancer Res. 12(13) (2006) 3979-84.

[31] E. Hasnis, M. Bar-Shai, Z. Burbea, A Z. Reznick, Cigarette smoke-induced NF-kappaB activation in human lymphocytes: the effect of low and high exposure to gas phase of cigarette smoke. J Physiol Pharmacol. 58 Suppl 5 (Pt 1) (2007) 263-274

[32] E. Hasnis, M. Bar-Shai, Z. Burbea, A Z. Reznick, Mechanisms underlying cigarette smoke-induced NF-kappaB activation in human lymphocytes: the role of reactive nitrogen species. J. Physiol. Pharmacol. 58 Suppl 5 (Pt 1) (2007), 275-87.

[33] M. Bar-Shai, E. Hasnis, Z. Wiener-Megnazi, A Z. Reznick, The role of reactive nitrogen species and cigarette smoke in activation of transcription factor NF-kappaB and implication to inflammatory processes. J. Physiol. Pharmacol. 57 Suppl 4 (2006) 39-44.

[34] O. Ben Izhak, F. Kablan, Z. Laster, R. M. Nagler, Oropharyngeal cancer pathogenesis: ubiquitin proteolytic, apoptotic and epidermal growth factor related pathways act in concert—first report, Oral Oncol. 41 (2005), 851-860.

[35] B. Chelli, A. Lena, R. Vanacore, E D. Pozzo, B. Costa, L. Rossi, A. Salvetti, F. Scatena, S. Ceruti, M P. Abbracchio, V. Gremigni, C. Martini, Peripheral benzodiazepine receptor ligands: mitochondrial transmembrane potential depolarization and apoptosis induction in rat C6 glioma cells. Biochem. Pharmacol, 68 (2004), 125-134.

[36] R. Nagler, D. Savulescu, E. Krayzler, S. Leschiner, L. Veenman, and M. Gavish, Cigarette smoke decreases salivary 18 kDa Translocator Protein binding affinity—in association with oxidative stress, Current Medical Chemistry (2010), in press.

[37] L. Veenman, J. Alten, K. Linnemannstons, Y. Shandalov, M. Lakomek, M. Gavish, W. Kugler, Potential involvement of $F_0F_1$-ATP(synth)ase and reactive oxygen species in apoptosis induction by the antineoplastic agent erucylphosphohomocholine in glioblastoma cell lines. Apoptosis (in press).

[38] L. Veenman, A. Weizman, G. Weisinger, M. Gavish, Expression and functions of the 18 kDa Mitochondrial Translocator Protein (TSPO) in Health and Disease. Targeted Drug Delivery in Cancer Therapeutics (2009) in press.

[39] L. Veenman, V. Papadopoulos, M. Gavish, Channel-like functions of the 18-kDa translocator protein (TSPO): regulation of apoptosis and steroidogenesis as part of the host-defense response, Curr. Pharm. Des. 13 (2007), 2385-2405.

[40] E. C. Pietsch, O. Humbey, M. E. Murphy, Polymorphisms in the p53 pathway, Oncogene 25 (2006), 1602-1611.

[41] W. Li, M. J. Hardwick, D. Rosenthal, M. Culty, V. Papadopoulos, Peripheral-type benzodiazepine receptor over-expression and knockdown in human breast cancer cells indicate its prominent role in tumor cell proliferation. Biochem Pharmacol. 15 (2007), 491-503.

[42] K. S. Panickar, A. R. Jayakumar, K. V. Rama Rao, M. D. Norenberg, Downregulation of the 18-kDa translocator protein: effects on the ammonia-induced mitochondrial permeability transition and cell swelling in cultured astrocytes. Glia. 55 (2007), 1720-1727.

[43] B. Chelli, A. Salvetti, E. Da Pozzo, M. Rechichi, F. Spinetti, L. Rossi, B. Costa, A. Lena, G. Rainaldi, F. Scatena, R. Vanacore, V. Gremigni, C. Martini, PK 11195 differentially affects cell survival in human wild-type and 18 kDa translocator protein-silenced ADF astrocytoma cells. J. Cell. Biochem. 105 (2008) 712-723.

[44] M. Rechichi, A. Salvetti, B. Chelli, B. Costa, E. Da Pozzo, F. Spinetti, A. Lena, M. Evangelista, G. Rainaldi, C. Martini, V. Gremigni, L. Rossi, TSPO over-expression increases motility, transmigration and proliferation properties of C6 rat glioma cells. Biochim. Biophys. Acta. 1782, (2008) 118-125.

[45] V. Papadopoulos, M. Baraldi, T. R. Guilarte, T. B. Knudsen, J. J. Lacapere, P. Lindemann, M. D. Norenberg, D. Nutt, A. Weizman, M. R. Zhang, M. Gavish, Translocator protein (18 kDa): new nomenclature for the peripheral-type benzodiazepine receptor based on its structure and molecular function. Trends Pharmacol Sci. 27 (2006) 402-409.

[46] A. J. Sasco, M. B. Secretan, K. Straif, Tobacco smoking and cancer: a brief review of recent epidemiological evidence, Lung Cancer 45 Suppl 2 (2004), S3-9.

[47] F. Delavoie, H. Li, M. Hardwick, J. Robert, C. Giatzakis, G. Peranzi, J. Maccario, J. Lacapere, V. Papadopoulos, In vivo and in vitro peripheral-type benzodiazepine receptor polymerization: functional significance in drug ligand and cholesterol binding. Biochem. 42 (2003), 4506-4519.

[48] A. Miyakawa, X. L. Wang, H. Nakanishi, F. L. Imai, M. Shiiba, T. Miya, Y. Imai, H. Tanzawa, Allelic loss on chromosome 22 in oral cancer: possibility of the existence of a tumor suppressor gene on 22q13, Int. J. Oncol. 13 (1998), 705-709.

[49] P. P. Reis, S. R. Rogatto, L. P. Kowalski, I. N. Nishimoto, J. C. Montovani, G. Corpus, J. A. Squire, S. Kamel-Reid, Quantitative real-time PCR identifies a critical region of deletion on 22q13 related to prognosis in oral cancer, Oncogene 21 (2002), 6480-6487.

[50] P. P. Dos Reis, R. C. Poli-Frederico, R. M. dos Santos, I. N. Nishimoto, L. P. Kowalski, S. R. Rogatto, Distinct regions of loss of heterozygosity on 22q in different sites of head and neck squamous cell carcinomas, Med. Sci. Monit. 8 (2002), BR89-94.

What is claimed is:

1. A method of diagnosing oral or oral-pharyngeal cancer in a subject in need thereof, the method comprising:
   (a) obtaining an unstimulated saliva sample from the subject,
   (b) contacting said saliva sample with at least one antibody capable of binding at least one saliva marker selected from the group consisting of Cyclin D1, phospho-Src, 8-oxoguanine DNA glycosylase (OGG1) Maspin and KI67,
   (c) determining a level of said at least one marker in said saliva sample of the subject by detection of antibody-marker immunocomplex,
   (d) comparing said level of said at least one marker with that of a saliva sample of an unaffected control sample, and
   (e) diagnosing oral or oral-pharyngeal cancer in said subject, wherein an increase in a level of Cyclin D1 or KI67, or a reduction in a level of any one of phospho-Src, 8-oxoguanine DNA glycosylase (OGG1) or Maspin, relative to said control is indicative of oral or oral pharyngeal cancer in said subject.

2. The method of claim 1, further comprising informing the subject of presence or absence of oral cancer following step (e).

3. The method of claim 1, further comprising corroborating said diagnosis using a diagnostic assay selected from the group comprising tissue biopsy, oral examination, dental X-ray, head X-ray, CT scan, ultrasonography and MRI.

4. The method of claim 1, wherein said oral cancer comprises oral squamous cell carcinoma.

5. The method of claim 1, wherein step (b) comprises contacting said unstimulated saliva sample with at least two antibodies, each capable of binding a different marker selected from the group consisting of markers selected from the group consisting of Cyclin D1, phospho-Src, 8-oxoguanine DNA glycosylase (OGG1), Maspin, KI67 and step (c) comprises determining the level of at least two markers selected from the group consisting of Cyclin D1, phospho-Src, 8-oxoguanine DNA glycosylase (OGG1), Maspin, KI67 by detection of the antibody-marker immunocomplex.

6. The method of claim 5, wherein step (b) comprises contacting said sample with an antibody capable of binding Maspin and an antibody capable of binding Cyclin D1 or with an antibody capable of binding Maspin and an antibody capable of binding OGG1, step (c) comprises determining the level of anti-Maspin-Maspin immunocomplex and anti-Cyclin D1-Cyclin D1 immunocomplex, or determining the level of anti-Maspin-Maspin immunocomplex and anti-OGG1-OGG1 immunocomplex wherein an increase in a level of Cyclin D1 and reduction in a level of Maspin or a reduction in a level of Maspin and OGG1, relative to said control is indicative of oral or oral pharyngeal cancer in said subject.

7. The method of claim 1, wherein said saliva sample is a cellular fraction of saliva.

8. The method of claim 1, wherein said determining is effected by Enzyme-linked immunosorbent assay (ELISA).

9. The method of claim 6, wherein said at least two markers are Cyclin D1 and Maspin.

10. The method of claim 6, wherein said at least two markers are Maspin and OGG1.

11. A method of diagnosing or determining a prognosis of oral cancer or oral pharyngeal cancer in a subject in need thereof, the method comprising:
   (a) obtaining an oral tissue biopsy sample from said subject;

(b) contacting the oral tissue biopsy sample with a translocator protein 18 kDa (TSPO)-specific antibody to produce an antibody-TSPO complex, (c) determining a level of TSPO in the sample by detection of the antibody-TSPO complex in said biopsy of the subject;

(d) comparing said level of the antibody-TSPO-complex with that of an oral tissue biopsy sample of an unaffected control, and (e) diagnosing or determining a prognosis of oral or oralpharyngeal cancer in said subject, wherein a significant increase in said level of said antibody-TSPO complex with respect to an unaffected oral tissue biopsy is indicative of the oral or oral pharyngeal cancer and is inversely correlated with a good prognosis.

12. The method of claim 11, further comprising corroborating said diagnosis using a diagnostic assay selected from the group comprising tissue biopsy, oral examination, dental X-ray, head X-ray, CT scan, ultrasonography and MRI.

13. The method of claim 11, wherein said oral cancer comprises oral squamous cell carcinoma.

* * * * *